United States Patent
Besko

(10) Patent No.: US 8,311,601 B2
(45) Date of Patent: Nov. 13, 2012

(54) REFLECTANCE AND/OR TRANSMISSIVE PULSE OXIMETER

(75) Inventor: David P. Besko, Thornton, CO (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 627 days.

(21) Appl. No.: 12/495,551

(22) Filed: Jun. 30, 2009

(65) Prior Publication Data

US 2010/0331638 A1    Dec. 30, 2010

(51) Int. Cl.
*A61B 5/1455* (2006.01)
(52) U.S. Cl. ......................... 600/323; 600/344
(58) Field of Classification Search ........... 600/309–344
See application file for complete search history.

(56) References Cited

U.S. PATENT DOCUMENTS

| | | | |
|---|---|---|---|
| 3,721,813 A | 3/1973 | Condon et al. |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |

(Continued)

FOREIGN PATENT DOCUMENTS

DE    19632361    2/1997

(Continued)

OTHER PUBLICATIONS

Rhee, Sokwoo, et al.; "The Ring Sensor: a New Ambulatory Wearable Sensor for Twenty-Four Hour Patient Monitoring," *Proceedings of the $20^{th}$ annual International Conference of the IEEE Engineering in Medicine and Biology Society*, vol. 20, No. 4, pp. 1906-1919.

(Continued)

*Primary Examiner* — Eric Winakur
*Assistant Examiner* — Marjan Fardanesh
(74) *Attorney, Agent, or Firm* — Fletcher Yoder

(57) ABSTRACT

According to various embodiments, a medical sensor assembly may be configured to switch between transmission and reflectance mode. Such sensors may include multiple optical sensing components that may be activated or silent, depending on the mode in use. A practitioner may switch between modes based on the particular situation of the patient or based on the signal quality.

16 Claims, 9 Drawing Sheets

U.S. PATENT DOCUMENTS

| | | |
|---|---|---|
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hausman et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,084,327 A | 1/1992 | Stengel |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,273,036 A | 12/1993 | Kronberg et al. |
| 5,275,159 A | 1/1994 | Griebel |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |
| 5,469,845 A | 11/1995 | DeLonzor et al. |
| RE35,122 E | 12/1995 | Corenman et al. |

| Patent No. | Date | Inventor(s) |
|---|---|---|
| 5,474,065 A | 12/1995 | Meathrel et al. |
| 5,482,034 A | 1/1996 | Lewis et al. |
| 5,482,036 A | 1/1996 | Diab et al. |
| 5,483,646 A | 1/1996 | Uchikoga |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,511,546 A | 4/1996 | Hon |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,595,176 A | 1/1997 | Yamaura |
| 5,596,986 A | 1/1997 | Goldfarb |
| 5,611,337 A | 3/1997 | Bukta |
| 5,617,852 A | 4/1997 | MacGregor |
| 5,619,992 A | 4/1997 | Guthrie et al. |
| 5,626,140 A | 5/1997 | Feldman et al. |
| 5,630,413 A | 5/1997 | Thomas et al. |
| 5,632,272 A | 5/1997 | Diab et al. |
| 5,632,273 A | 5/1997 | Suzuki |
| 5,634,459 A | 6/1997 | Gardosi |
| 5,638,593 A | 6/1997 | Gerhardt et al. |
| 5,638,818 A | 6/1997 | Diab et al. |
| 5,645,060 A | 7/1997 | Yorkey |
| 5,645,440 A | 7/1997 | Tobler et al. |
| 5,660,567 A | 8/1997 | Nierlich et al. |
| 5,662,105 A | 9/1997 | Tien |
| 5,662,106 A | 9/1997 | Swedlow et al. |
| 5,666,952 A | 9/1997 | Fuse et al. |
| 5,671,529 A | 9/1997 | Nelson |
| 5,673,692 A | 10/1997 | Schulze et al. |
| 5,673,693 A | 10/1997 | Solenberger |
| 5,676,139 A | 10/1997 | Goldberger et al. |
| 5,676,141 A | 10/1997 | Hollub |
| 5,678,544 A | 10/1997 | DeLonzor et al. |
| 5,680,857 A | 10/1997 | Pelikan et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,692,503 A | 12/1997 | Kuenstner |
| 5,692,505 A | 12/1997 | Fouts |
| 5,709,205 A | 1/1998 | Bukta |
| 5,713,355 A | 2/1998 | Richardson et al. |
| 5,724,967 A | 3/1998 | Venkatachalam |
| 5,727,547 A | 3/1998 | Levinson et al. |
| 5,731,582 A | 3/1998 | West |
| D393,830 S | 4/1998 | Tobler et al. |
| 5,743,260 A | 4/1998 | Chung et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | DeLonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,766,125 A | 6/1998 | Aoyagi et al. |
| 5,766,127 A | 6/1998 | Pologe et al. |
| 5,769,785 A | 6/1998 | Diab et al. |
| 5,772,587 A | 6/1998 | Gratton et al. |
| 5,774,213 A | 6/1998 | Trebino et al. |
| 5,776,058 A | 7/1998 | Levinson et al. |
| 5,776,059 A | 7/1998 | Kaestle |
| 5,779,630 A | 7/1998 | Fein et al. |
| 5,779,631 A | 7/1998 | Chance |
| 5,782,237 A | 7/1998 | Casciani et al. |
| 5,782,756 A | 7/1998 | Mannheimer |
| 5,782,757 A | 7/1998 | Diab et al. |
| 5,782,758 A | 7/1998 | Ausec et al. |
| 5,786,592 A | 7/1998 | Hök |
| 5,790,729 A | 8/1998 | Pologe et al. |
| 5,792,052 A | 8/1998 | Isaacson et al. |
| 5,795,292 A | 8/1998 | Lewis et al. |
| 5,797,841 A | 8/1998 | DeLonzor et al. |
| 5,800,348 A | 9/1998 | Kaestle |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,807,248 A | 9/1998 | Mills |
| 5,810,723 A | 9/1998 | Aldrich |
| 5,810,724 A | 9/1998 | Gronvall |
| 5,813,980 A | 9/1998 | Levinson et al. |
| 5,817,008 A | 10/1998 | Rafert et al. |
| 5,817,009 A | 10/1998 | Rosenheimer et al. |
| 5,817,010 A | 10/1998 | Hibl |
| 5,818,985 A | 10/1998 | Merchant et al. |
| 5,820,550 A | 10/1998 | Polson et al. |
| 5,823,950 A | 10/1998 | Diab et al. |
| 5,823,952 A | 10/1998 | Levinson et al. |
| 5,827,182 A | 10/1998 | Raley et al. |
| 5,830,135 A | 11/1998 | Bosque et al. |
| 5,830,136 A | 11/1998 | DeLonzor et al. |
| 5,830,137 A | 11/1998 | Scharf |
| 5,839,439 A | 11/1998 | Nierlich et al. |
| RE36,000 E | 12/1998 | Swedlow et al. |
| 5,842,979 A | 12/1998 | Jarman et al. |
| 5,842,981 A | 12/1998 | Larsen et al. |
| 5,842,982 A | 12/1998 | Mannheimer |
| 5,846,190 A | 12/1998 | Woehrle |
| 5,851,178 A | 12/1998 | Aronow |
| 5,851,179 A | 12/1998 | Ritson et al. |
| 5,853,364 A | 12/1998 | Baker, Jr. et al. |
| 5,860,919 A | 1/1999 | Kiani-Azarbayjany et al. |
| 5,865,736 A | 2/1999 | Baker, Jr. et al. |
| 5,871,442 A | 2/1999 | Madarasz et al. |
| 5,879,294 A | 3/1999 | Anderson et al. |
| 5,885,213 A | 3/1999 | Richardson et al. |
| 5,890,929 A | 4/1999 | Mills et al. |
| 5,891,021 A | 4/1999 | Dillon et al. |
| 5,891,022 A | 4/1999 | Pologe |
| 5,891,024 A | 4/1999 | Jarman et al. |
| 5,891,025 A | 4/1999 | Buschmann et al. |
| 5,891,026 A | 4/1999 | Wang et al. |
| 5,902,235 A | 5/1999 | Lewis et al. |
| 5,910,108 A | 6/1999 | Solenberger |
| 5,911,690 A | 6/1999 | Rall |
| 5,912,656 A | 6/1999 | Tham et al. |
| 5,913,819 A | 6/1999 | Taylor et al. |
| 5,916,154 A | 6/1999 | Hobbs et al. |
| 5,916,155 A | 6/1999 | Levinson et al. |
| 5,919,133 A | 7/1999 | Taylor et al. |
| 5,919,134 A | 7/1999 | Diab |
| 5,920,263 A | 7/1999 | Huttenhoff et al. |
| 5,921,921 A | 7/1999 | Potratz et al. |
| 5,922,607 A | 7/1999 | Bernreuter |
| 5,924,979 A | 7/1999 | Swedlow et al. |
| 5,924,980 A | 7/1999 | Coetzee |
| 5,924,982 A | 7/1999 | Chin |
| 5,924,985 A | 7/1999 | Jones |
| 5,934,277 A | 8/1999 | Mortz |

| | | | |
|---|---|---|---|
| 5,934,925 A | 8/1999 | Tobler et al. |
| 5,940,182 A | 8/1999 | Lepper, Jr. et al. |
| 5,954,644 A | 9/1999 | Dettling et al. |
| 5,960,610 A | 10/1999 | Levinson et al. |
| 5,961,450 A | 10/1999 | Merchant et al. |
| 5,961,452 A | 10/1999 | Chung et al. |
| 5,964,701 A | 10/1999 | Asada et al. |
| 5,971,930 A | 10/1999 | Elghazzawi |
| 5,978,691 A | 11/1999 | Mills |
| 5,978,693 A | 11/1999 | Hamilton et al. |
| 5,983,122 A | 11/1999 | Jarman et al. |
| 5,987,343 A | 11/1999 | Kinast |
| 5,991,648 A | 11/1999 | Levin |
| 5,995,855 A | 11/1999 | Kiani et al. |
| 5,995,856 A | 11/1999 | Mannheimer et al. |
| 5,995,858 A | 11/1999 | Kinast |
| 5,995,859 A | 11/1999 | Takahashi |
| 5,997,343 A | 12/1999 | Mills et al. |
| 5,999,834 A | 12/1999 | Wang et al. |
| 6,002,952 A | 12/1999 | Diab et al. |
| 6,005,658 A | 12/1999 | Kaluza et al. |
| 6,006,120 A | 12/1999 | Levin |
| 6,011,985 A | 1/2000 | Athan et al. |
| 6,011,986 A | 1/2000 | Diab et al. |
| 6,014,576 A | 1/2000 | Raley et al. |
| 6,018,673 A | 1/2000 | Chin et al. |
| 6,018,674 A | 1/2000 | Aronow |
| 6,022,321 A | 2/2000 | Amano et al. |
| 6,023,541 A | 2/2000 | Merchant et al. |
| 6,026,312 A | 2/2000 | Shemwell et al. |
| 6,026,314 A | 2/2000 | Amerov et al. |
| 6,031,603 A | 2/2000 | Fine et al. |
| 6,035,223 A | 3/2000 | Baker, Jr. |
| 6,036,642 A | 3/2000 | Diab et al. |
| 6,041,247 A | 3/2000 | Weckstrom et al. |
| 6,044,283 A | 3/2000 | Fein et al. |
| 6,047,201 A | 4/2000 | Jackson, III |
| 6,061,584 A | 5/2000 | Lovejoy et al. |
| 6,064,898 A | 5/2000 | Aldrich |
| 6,064,899 A | 5/2000 | Fein et al. |
| 6,067,462 A | 5/2000 | Diab et al. |
| 6,073,038 A | 6/2000 | Wang et al. |
| 6,078,833 A | 6/2000 | Hueber |
| 6,081,735 A | 6/2000 | Diab et al. |
| 6,081,742 A | 6/2000 | Amano et al. |
| 6,083,157 A | 7/2000 | Noller |
| 6,083,172 A | 7/2000 | Baker, Jr. et al. |
| 6,088,607 A | 7/2000 | Diab et al. |
| 6,094,592 A | 7/2000 | Yorkey et al. |
| 6,095,974 A | 8/2000 | Shemwell et al. |
| 6,104,938 A | 8/2000 | Huiku et al. |
| 6,112,107 A | 8/2000 | Hannula |
| 6,113,541 A | 9/2000 | Dias et al. |
| 6,115,621 A | 9/2000 | Chin |
| 6,122,535 A | 9/2000 | Kaestle et al. |
| 6,133,994 A | 10/2000 | Mathews et al. |
| 6,135,952 A | 10/2000 | Coetzee |
| 6,144,444 A | 11/2000 | Haworth et al. |
| 6,144,867 A | 11/2000 | Walker et al. |
| 6,144,868 A | 11/2000 | Parker |
| 6,149,481 A | 11/2000 | Wang et al. |
| 6,150,951 A | 11/2000 | Olejniczak |
| 6,151,107 A | 11/2000 | Schöllermann et al. |
| 6,151,518 A | 11/2000 | Hayashi |
| 6,152,754 A | 11/2000 | Gerhardt et al. |
| 6,154,667 A | 11/2000 | Miura et al. |
| 6,157,850 A | 12/2000 | Diab et al. |
| 6,163,715 A | 12/2000 | Larsen et al. |
| 6,165,005 A | 12/2000 | Mills et al. |
| 6,173,196 B1 | 1/2001 | Delonzor et al. |
| 6,178,343 B1 | 1/2001 | Bindszus et al. |
| 6,181,958 B1 | 1/2001 | Steuer et al. |
| 6,181,959 B1 | 1/2001 | Schöllermann et al. |
| 6,184,521 B1 | 2/2001 | Coffin, IV et al. |
| 6,188,470 B1 | 2/2001 | Grace |
| 6,192,260 B1 | 2/2001 | Chance |
| 6,195,575 B1 | 2/2001 | Levinson |
| 6,198,951 B1 | 3/2001 | Kosuda et al. |
| 6,206,830 B1 | 3/2001 | Diab et al. |
| 6,213,952 B1 | 4/2001 | Finarov et al. |
| 6,217,523 B1 | 4/2001 | Amano et al. |
| 6,222,189 B1 | 4/2001 | Misner et al. |
| 6,226,539 B1 | 5/2001 | Potratz |
| 6,226,540 B1 | 5/2001 | Bernreuter et al. |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grimblatov |
| 6,263,221 B1 | 7/2001 | Chance et al. |
| 6,263,222 B1 | 7/2001 | Diab et al. |
| 6,263,223 B1 | 7/2001 | Shepherd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura et al. |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| 6,370,408 B1 | 4/2002 | Merchant et al. |
| 6,370,409 B1 | 4/2002 | Chung et al. |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenstner |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,419,671 B1 | 7/2002 | Lemberg |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |

| | | | | | | |
|---|---|---|---|---|---|---|
| 6,470,199 B1 | 10/2002 | Kopotic et al. | | 6,681,126 B2 | 1/2004 | Solenberger |
| 6,470,200 B2 | 10/2002 | Walker et al. | | 6,681,128 B2 | 1/2004 | Steuer et al. |
| 6,480,729 B2 | 11/2002 | Stone | | 6,681,454 B2 | 1/2004 | Modgil et al. |
| 6,490,466 B1 | 12/2002 | Fein et al. | | 6,684,090 B2 | 1/2004 | Ali et al. |
| 6,496,711 B1 | 12/2002 | Athan et al. | | 6,684,091 B2 | 1/2004 | Parker |
| 6,498,942 B1 | 12/2002 | Esenaliev et al. | | 6,694,160 B2 | 2/2004 | Chin |
| 6,501,974 B2 | 12/2002 | Huiku | | 6,697,653 B2 | 2/2004 | Hanna |
| 6,501,975 B2 | 12/2002 | Diab et al. | | 6,697,655 B2 | 2/2004 | Sueppel et al. |
| 6,505,060 B1 | 1/2003 | Norris | | 6,697,656 B1 | 2/2004 | Al-Ali |
| 6,505,061 B2 | 1/2003 | Larson | | 6,697,658 B2 | 2/2004 | Al-Ali |
| 6,505,133 B1 | 1/2003 | Hanna et al. | | RE38,476 E | 3/2004 | Diab et al. |
| 6,510,329 B2 | 1/2003 | Heckel | | 6,699,194 B1 | 3/2004 | Diab et al. |
| 6,510,331 B1 | 1/2003 | Williams et al. | | 6,699,199 B2 | 3/2004 | Asada et al. |
| 6,512,937 B2 | 1/2003 | Blank et al. | | 6,701,170 B2 | 3/2004 | Stetson |
| 6,515,273 B2 | 2/2003 | Al-Ali | | 6,702,752 B2 | 3/2004 | Dekker |
| 6,519,484 B1 | 2/2003 | Lovejoy et al. | | 6,707,257 B2 | 3/2004 | Norris |
| 6,519,486 B1 | 2/2003 | Edgar, Jr. et al. | | 6,708,049 B1 | 3/2004 | Berson et al. |
| 6,519,487 B1 | 2/2003 | Parker | | 6,709,402 B2 | 3/2004 | Dekker |
| 6,525,386 B1 | 2/2003 | Mills et al. | | 6,711,424 B1 | 3/2004 | Fine et al. |
| 6,526,300 B1 | 2/2003 | Kiani et al. | | 6,711,425 B1 | 3/2004 | Reuss |
| 6,526,301 B2 | 2/2003 | Larsen et al. | | 6,714,803 B1 | 3/2004 | Mortz |
| 6,541,756 B2 | 4/2003 | Schulz et al. | | 6,714,804 B2 | 3/2004 | Al-Ali et al. |
| 6,542,764 B1 | 4/2003 | Al-Ali et al. | | 6,714,805 B2 | 3/2004 | Jeon et al. |
| 6,546,267 B1 | 4/2003 | Sugiura et al. | | RE38,492 E | 4/2004 | Diab et al. |
| 6,553,241 B2 | 4/2003 | Mannheimer et al. | | 6,719,686 B2 | 4/2004 | Coakley et al. |
| 6,553,242 B1 | 4/2003 | Sarussi | | 6,719,705 B2 | 4/2004 | Mills |
| 6,553,243 B2 | 4/2003 | Gurley | | 6,720,734 B2 | 4/2004 | Norris |
| 6,556,852 B1 | 4/2003 | Schulze et al. | | 6,721,584 B2 | 4/2004 | Baker, Jr. et al. |
| 6,560,470 B1 | 5/2003 | Pologe | | 6,721,585 B1 | 4/2004 | Parker |
| 6,564,077 B2 | 5/2003 | Mortara | | 6,725,074 B1 | 4/2004 | Kästle |
| 6,564,088 B1 | 5/2003 | Soller et al. | | 6,725,075 B2 | 4/2004 | Al-Ali |
| 6,571,113 B1 | 5/2003 | Fein et al. | | 6,731,963 B2 | 5/2004 | Finarov et al. |
| 6,571,114 B1 | 5/2003 | Koike et al. | | 6,731,967 B1 | 5/2004 | Turcott |
| 6,574,491 B2 | 6/2003 | Elghazzawi | | 6,735,459 B2 | 5/2004 | Parker |
| 6,580,086 B1 | 6/2003 | Schulz et al. | | 6,745,060 B2 | 6/2004 | Diab et al. |
| 6,584,336 B1 | 6/2003 | Ali et al. | | 6,745,061 B1 | 6/2004 | Hicks et al. |
| 6,587,703 B2 | 7/2003 | Cheng et al. | | 6,748,253 B2 | 6/2004 | Norris et al. |
| 6,587,704 B1 | 7/2003 | Fine et al. | | 6,748,254 B2 | 6/2004 | O'Neil et al. |
| 6,589,172 B2 | 7/2003 | Williams et al. | | 6,754,515 B1 | 6/2004 | Pologe |
| 6,591,122 B2 | 7/2003 | Schmitt | | 6,754,516 B2 | 6/2004 | Mannheimer |
| 6,591,123 B2 | 7/2003 | Fein et al. | | 6,760,607 B2 | 7/2004 | Al-All |
| 6,594,511 B2 | 7/2003 | Stone et al. | | 6,760,609 B2 | 7/2004 | Jacques |
| 6,594,512 B2 | 7/2003 | Huang | | 6,760,610 B2 | 7/2004 | Tscupp et al. |
| 6,594,513 B1 | 7/2003 | Jobsis et al. | | 6,763,255 B2 | 7/2004 | DeLonzor et al. |
| 6,597,931 B1 | 7/2003 | Cheng et al. | | 6,763,256 B2 | 7/2004 | Kimball et al. |
| 6,597,933 B2 | 7/2003 | Kiani et al. | | 6,770,028 B1 | 8/2004 | Ali et al. |
| 6,600,940 B1 | 7/2003 | Fein et al. | | 6,771,994 B2 | 8/2004 | Kiani et al. |
| 6,606,510 B2 | 8/2003 | Swedlow et al. | | 6,773,397 B2 | 8/2004 | Kelly |
| 6,606,511 B1 | 8/2003 | Ali et al. | | 6,778,923 B2 | 8/2004 | Norris et al. |
| 6,606,512 B2 | 8/2003 | Muz et al. | | 6,780,158 B2 | 8/2004 | Yarita |
| 6,615,064 B1 | 9/2003 | Aldrich | | 6,791,689 B1 | 9/2004 | Weckström |
| 6,615,065 B1 | 9/2003 | Barrett et al. | | 6,792,300 B1 | 9/2004 | Diab et al. |
| 6,618,602 B2 | 9/2003 | Levin | | 6,793,654 B2 | 9/2004 | Lemberg |
| 6,622,034 B1 | 9/2003 | Gorski et al. | | 6,801,797 B2 | 10/2004 | Mannheimer et al. |
| 6,628,975 B1 | 9/2003 | Fein et al. | | 6,801,798 B2 | 10/2004 | Geddes et al. |
| 6,631,281 B1 | 10/2003 | Kästle | | 6,801,799 B2 | 10/2004 | Mendelson |
| 6,643,530 B2 | 11/2003 | Diab et al. | | 6,801,802 B2 | 10/2004 | Sitzman et al. |
| 6,643,531 B1 | 11/2003 | Katarow | | 6,802,812 B1 | 10/2004 | Walker et al. |
| 6,647,279 B2 | 11/2003 | Pologe | | 6,805,673 B2 | 10/2004 | Dekker |
| 6,647,280 B2 | 11/2003 | Bahr et al. | | 6,810,277 B2 | 10/2004 | Edgar, Jr. et al. |
| 6,650,917 B2 | 11/2003 | Diab et al. | | 6,813,511 B2 | 11/2004 | Diab et al. |
| 6,650,918 B2 | 11/2003 | Terry | | 6,816,741 B2 | 11/2004 | Diab |
| 6,654,621 B2 | 11/2003 | Palatnik et al. | | 6,819,950 B2 | 11/2004 | Mills |
| 6,654,622 B1 | 11/2003 | Eberhard et al. | | 6,822,564 B2 | 11/2004 | Al-Ali |
| 6,654,623 B1 | 11/2003 | Kästle | | 6,825,619 B2 | 11/2004 | Norris |
| 6,654,624 B2 | 11/2003 | Diab et al. | | 6,826,419 B2 | 11/2004 | Diab et al. |
| 6,658,276 B2 | 12/2003 | Kianl et al. | | 6,829,496 B2 | 12/2004 | Nagai et al. |
| 6,658,277 B2 | 12/2003 | Wasserman | | 6,830,711 B2 | 12/2004 | Mills et al. |
| 6,662,033 B2 | 12/2003 | Casciani et al. | | 6,836,679 B2 | 12/2004 | Baker, Jr. et al. |
| 6,665,551 B1 | 12/2003 | Suzuki | | 6,839,579 B1 | 1/2005 | Chin |
| 6,668,182 B2 | 12/2003 | Hubelbank | | 6,839,580 B2 | 1/2005 | Zonios et al. |
| 6,668,183 B2 | 12/2003 | Hicks et al. | | 6,839,582 B2 | 1/2005 | Heckel |
| 6,671,526 B1 | 12/2003 | Aoyagi et al. | | 6,839,659 B2 | 1/2005 | Tarassenko et al. |
| 6,671,528 B2 | 12/2003 | Steuer et al. | | 6,842,635 B1 | 1/2005 | Parker |
| 6,671,530 B2 | 12/2003 | Chung et al. | | 6,845,256 B2 | 1/2005 | Chin et al. |
| 6,671,531 B2 | 12/2003 | Al-Ali et al. | | 6,850,787 B2 | 2/2005 | Weber et al. |
| 6,671,532 B1 | 12/2003 | Fudge et al. | | 6,850,788 B2 | 2/2005 | Al-Ali |
| 6,675,031 B1 | 1/2004 | Porges et al. | | 6,850,789 B2 | 2/2005 | Schweitzer, Jr. et al. |
| 6,678,543 B2 | 1/2004 | Diab et al. | | 6,861,639 B2 | 3/2005 | Al-Ali |

| | | | | | |
|---|---|---|---|---|---|
| 6,863,652 B2 | 3/2005 | Huang et al. | 2001/0051767 A1 | 12/2001 | Williams et al. |
| 6,865,407 B2 | 3/2005 | Kimball et al. | 2002/0026109 A1 | 2/2002 | Diab et al. |
| 6,879,850 B2 | 4/2005 | Kimball | 2002/0028990 A1 | 3/2002 | Shepherd et al. |
| 6,882,874 B2 | 4/2005 | Huiku | 2002/0038078 A1 | 3/2002 | Ito |
| 6,889,153 B2 | 5/2005 | Dietiker | 2002/0042558 A1 | 4/2002 | Mendelson |
| 6,898,452 B2 | 5/2005 | Al-Ali et al. | 2002/0068859 A1 | 6/2002 | Knopp |
| 6,909,912 B2 | 6/2005 | Melker et al. | 2002/0128544 A1 | 9/2002 | Diab et al. |
| 6,912,413 B2 | 6/2005 | Rantala et al. | 2002/0133067 A1 | 9/2002 | Jackson, III |
| 6,916,289 B2 | 7/2005 | Schnall | 2002/0156354 A1 | 10/2002 | Larson |
| 6,920,345 B2 | 7/2005 | Al-Ali et al. | 2002/0173706 A1 | 11/2002 | Takatani |
| 6,931,269 B2 | 8/2005 | Terry | 2002/0173709 A1 | 11/2002 | Fine et al. |
| 6,934,570 B2 | 8/2005 | Kiani et al. | 2002/0190863 A1 | 12/2002 | Lynn |
| 6,939,307 B1 | 9/2005 | Dunlop | 2002/0198442 A1 | 12/2002 | Rantala et al. |
| 6,941,162 B2 | 9/2005 | Fudge et al. | 2003/0018243 A1 | 1/2003 | Gerhardt et al. |
| 6,947,781 B2 | 9/2005 | Asada et al. | 2003/0036690 A1 | 2/2003 | Geddes et al. |
| 6,950,687 B2 | 9/2005 | Al-Ali | 2003/0045785 A1 | 3/2003 | Diab et al. |
| 6,963,767 B2 | 11/2005 | Rantala et al. | 2003/0073889 A1 | 4/2003 | Keilbach et al. |
| 6,971,580 B2 | 12/2005 | DeLonzor et al. | 2003/0073890 A1 | 4/2003 | Hanna |
| 6,983,178 B2 | 1/2006 | Fine et al. | 2003/0100840 A1 | 5/2003 | Sugiura et al. |
| 6,985,763 B2 | 1/2006 | Boas et al. | 2003/0132495 A1 | 7/2003 | Mills et al. |
| 6,985,764 B2 | 1/2006 | Mason et al. | 2003/0135099 A1 | 7/2003 | Al-Ali |
| 6,990,426 B2 | 1/2006 | Yoon et al. | 2003/0162414 A1 | 8/2003 | Schulz et al. |
| 6,992,751 B2 | 1/2006 | Al-Ali | 2003/0171662 A1 | 9/2003 | O'Connor et al. |
| 6,992,772 B2 | 1/2006 | Block et al. | 2003/0176776 A1 | 9/2003 | Huiku |
| 6,993,371 B2 | 1/2006 | Kiani et al. | 2003/0181799 A1 | 9/2003 | Lindekugel et al. |
| 6,993,372 B2 | 1/2006 | Fine et al. | 2003/0187337 A1 | 10/2003 | Tarassenko et al. |
| 6,996,427 B2 | 2/2006 | Ali et al. | 2003/0195402 A1 | 10/2003 | Fein et al. |
| 7,003,338 B2 | 2/2006 | Weber et al. | 2003/0197679 A1 | 10/2003 | Ali et al. |
| 7,003,339 B2 | 2/2006 | Diab et al. | 2003/0212316 A1 | 11/2003 | Leiden et al. |
| 7,006,855 B1 | 2/2006 | Sarussi | 2003/0225323 A1 | 12/2003 | Kiani et al. |
| 7,006,856 B2 | 2/2006 | Baker, Jr. et al. | 2003/0225337 A1 | 12/2003 | Scharf et al. |
| 7,016,715 B2 | 3/2006 | Stetson | 2003/0236452 A1 | 12/2003 | Melker et al. |
| 7,020,507 B2 | 3/2006 | Scharf et al. | 2003/0236647 A1 | 12/2003 | Yoon et al. |
| 7,024,233 B2 | 4/2006 | Ali et al. | 2004/0006261 A1 | 1/2004 | Swedlow et al. |
| 7,024,235 B2 | 4/2006 | Melker et al. | 2004/0010188 A1 | 1/2004 | Wasserman et al. |
| 7,025,728 B2 | 4/2006 | Ito et al. | 2004/0024297 A1 | 2/2004 | Chen et al. |
| 7,027,849 B2 | 4/2006 | Al-Ali et al. | 2004/0024326 A1 | 2/2004 | Yeo et al. |
| 7,027,850 B2 | 4/2006 | Wasserman | 2004/0034293 A1 | 2/2004 | Kimball |
| 7,035,697 B1 | 4/2006 | Brown | 2004/0039272 A1 | 2/2004 | Abdul-Hafiz et al. |
| 7,039,449 B2 | 5/2006 | Al-Ali | 2004/0039273 A1 | 2/2004 | Terry |
| 7,043,289 B2 | 5/2006 | Fine et al. | 2004/0054269 A1 | 3/2004 | Rantala et al. |
| 7,047,055 B2 | 5/2006 | Boaz et al. | 2004/0054291 A1 | 3/2004 | Schulz et al. |
| 7,047,056 B2 | 5/2006 | Hannula et al. | 2004/0059209 A1 | 3/2004 | Al-Ali et al. |
| 7,060,035 B2 | 6/2006 | Wasserman | 2004/0059210 A1 | 3/2004 | Stetson |
| 7,062,307 B2 | 6/2006 | Norris et al. | 2004/0064020 A1 | 4/2004 | Diab et al. |
| 7,067,893 B2 | 6/2006 | Mills et al. | 2004/0068164 A1 | 4/2004 | Diab et al. |
| 7,072,701 B2 | 7/2006 | Chen et al. | 2004/0087846 A1 | 5/2004 | Wasserman |
| 7,072,702 B2 | 7/2006 | Edgar, Jr. et al. | 2004/0092805 A1 | 5/2004 | Yarita |
| 7,079,880 B2 | 7/2006 | Stetson | 2004/0097797 A1 | 5/2004 | Porges et al. |
| 7,085,597 B2 | 8/2006 | Fein et al. | 2004/0098009 A1 | 5/2004 | Boecker et al. |
| 7,096,052 B2 | 8/2006 | Mason et al. | 2004/0107065 A1 | 6/2004 | Al-Ali et al. |
| 7,096,054 B2 | 8/2006 | Abdul-Hafiz et al. | 2004/0116788 A1 | 6/2004 | Chernoguz et al. |
| 7,107,088 B2 | 9/2006 | Aceti | 2004/0116789 A1 | 6/2004 | Boaz et al. |
| 7,113,815 B2 | 9/2006 | O'Neil et al. | 2004/0117891 A1 | 6/2004 | Hannula et al. |
| 7,123,950 B2 | 10/2006 | Mannheimer | 2004/0122300 A1 | 6/2004 | Boas et al. |
| 7,127,278 B2 | 10/2006 | Melker et al. | 2004/0122302 A1 | 6/2004 | Mason et al. |
| 7,130,671 B2 | 10/2006 | Baker, Jr. et al. | 2004/0133087 A1 | 7/2004 | Ali et al. |
| 7,132,641 B2 | 11/2006 | Schulz et al. | 2004/0133088 A1 | 7/2004 | Al-Ali et al. |
| 7,133,711 B2 | 11/2006 | Chernoguz et al. | 2004/0138538 A1 | 7/2004 | Stetson |
| 7,139,599 B2 | 11/2006 | Terry | 2004/0138540 A1 | 7/2004 | Baker, Jr. et al. |
| 7,142,901 B2 | 11/2006 | Kiani et al. | 2004/0143172 A1 | 7/2004 | Fudge et al. |
| 7,162,288 B2 | 1/2007 | Nordstrom | 2004/0147821 A1 | 7/2004 | Al-Ali et al. |
| 7,190,987 B2 | 3/2007 | Lindekugel et al. | 2004/0147822 A1 | 7/2004 | Al-Ali et al. |
| 7,198,778 B2 | 4/2007 | Mannheimer et al. | 2004/0147823 A1 | 7/2004 | Kiani et al. |
| 7,209,775 B2 | 4/2007 | Bae et al. | 2004/0147824 A1 | 7/2004 | Diab et al. |
| 7,215,984 B2 | 5/2007 | Diab et al. | 2004/0152965 A1 | 8/2004 | Diab et al. |
| 7,225,006 B2 | 5/2007 | Al-Ali et al. | 2004/0158134 A1 | 8/2004 | Diab et al. |
| 7,236,811 B2 | 6/2007 | Schmitt | 2004/0158135 A1 | 8/2004 | Baker, Jr. et al. |
| 7,248,910 B2 | 7/2007 | Li et al. | 2004/0162472 A1 | 8/2004 | Berson et al. |
| 7,254,433 B2 | 8/2007 | Diab et al. | 2004/0171920 A1 | 9/2004 | Mannheimer et al. |
| 7,254,434 B2 | 8/2007 | Schulz et al. | 2004/0171948 A1 | 9/2004 | Terry |
| 7,263,395 B2 | 8/2007 | Chan et al. | 2004/0176671 A1 | 9/2004 | Fine et al. |
| 7,272,425 B2 | 9/2007 | Al-Ali | 2004/0181133 A1 | 9/2004 | Al-Ali et al. |
| 7,272,426 B2 | 9/2007 | Scmid | 2004/0181134 A1 | 9/2004 | Baker, Jr. et al. |
| 7,280,858 B2 | 10/2007 | Al-Ali et al. | 2004/0186358 A1 | 9/2004 | Chernow et al. |
| 7,295,866 B2 | 11/2007 | Al-Ali et al. | 2004/0199063 A1 | 10/2004 | O'Neil et al. |
| 7,305,262 B2 | 12/2007 | Brodnick et al. | 2004/0204636 A1 | 10/2004 | Diab et al. |
| 7,315,753 B2 | 1/2008 | Baker, Jr. et al. | 2004/0204637 A1 | 10/2004 | Diab et al. |
| 2001/0021803 A1 | 9/2001 | Blank et al. | 2004/0204638 A1 | 10/2004 | Diab et al. |

| Publication No. | Date | Inventor |
|---|---|---|
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block et al. |
| 2004/0260161 A1 | 12/2004 | Melker et al. |
| 2004/0267103 A1 | 12/2004 | Li et al. |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0020887 A1 | 1/2005 | Goldberg |
| 2005/0020894 A1 | 1/2005 | Norris et al. |
| 2005/0033128 A1 | 2/2005 | Ali et al. |
| 2005/0033129 A1 | 2/2005 | Edgar, Jr. et al. |
| 2005/0043599 A1 | 2/2005 | O'Mara |
| 2005/0043600 A1 | 2/2005 | Diab et al. |
| 2005/0049470 A1 | 3/2005 | Terry |
| 2005/0049471 A1 | 3/2005 | Aceti |
| 2005/0075550 A1 | 4/2005 | Lindekugel |
| 2005/0113651 A1 | 5/2005 | Wood et al. |
| 2005/0177034 A1 | 8/2005 | Beaumont |
| 2005/0197548 A1 | 9/2005 | Dietiker |
| 2005/0197793 A1 | 9/2005 | Baker, Jr. |
| 2005/0228248 A1 | 10/2005 | Dietiker |
| 2005/0277819 A1 | 12/2005 | Kiani et al. |
| 2005/0283059 A1 | 12/2005 | Iyer et al. |
| 2006/0009685 A1 | 1/2006 | Finarov |
| 2006/0036136 A1 | 2/2006 | Shaw |
| 2006/0058594 A1 | 3/2006 | Ishizuka et al. |
| 2006/0084852 A1 | 4/2006 | Mason et al. |
| 2006/0089547 A1 | 4/2006 | Sarussi |
| 2006/0106294 A1 | 5/2006 | Maser et al. |
| 2006/0195028 A1 | 8/2006 | Hannula et al. |
| 2006/0200018 A1 | 9/2006 | Al-Ali |
| 2006/0224058 A1 | 10/2006 | Mannheimer |
| 2006/0247501 A1 | 11/2006 | Ali |
| 2006/0258921 A1 | 11/2006 | Addison et al. |
| 2006/0276700 A1 | 12/2006 | O'Neil |
| 2007/0032710 A1 | 2/2007 | Raridan et al. |
| 2007/0032712 A1 | 2/2007 | Raridan et al. |
| 2007/0032715 A1 | 2/2007 | Eghbal et al. |
| 2007/0073121 A1 | 3/2007 | Hoarau et al. |
| 2007/0073125 A1 | 3/2007 | Hoarau et al. |
| 2007/0073126 A1 | 3/2007 | Raridan, Jr. |
| 2007/0073128 A1 | 3/2007 | Hoarau et al. |
| 2007/0100220 A1 | 5/2007 | Baker, Jr. |
| 2008/0033267 A1 | 2/2008 | Al-Ali |
| 2008/0076987 A1 | 3/2008 | Arizaga |
| 2008/0221413 A1 | 9/2008 | Hoarau |
| 2009/0054751 A1 | 2/2009 | Babashan |

FOREIGN PATENT DOCUMENTS

| | | |
|---|---|---|
| EP | 0127947 | 12/1984 |
| EP | 0204259 | 12/1986 |
| EP | 0531631 | 3/1993 |
| EP | 0724860 | 8/1996 |
| FR | 2685865 | 7/1993 |
| JP | 2111343 | 4/1990 |
| JP | 3116259 | 12/1991 |
| JP | 3116260 | 12/1991 |
| JP | 5049625 | 3/1993 |
| JP | 6014906 | 1/1994 |
| JP | 7001273 | 1/1995 |
| JP | 7236625 | 9/1995 |
| JP | 10337282 | 12/1998 |
| JP | 2000237170 | 9/2000 |
| JP | 2004089546 | 3/2004 |
| JP | 2004159810 | 6/2004 |
| JP | 2004248820 | 9/2004 |
| JP | 2004329406 | 11/2004 |
| JP | 2004337605 | 12/2004 |
| JP | 2004344367 | 12/2004 |
| JP | 2004351107 | 12/2004 |
| WO | WO8909566 | 10/1989 |
| WO | WO9001293 | 2/1990 |
| WO | WO9502358 | 1/1995 |
| WO | 9637259 A1 | 11/1996 |
| WO | WO9736536 | 10/1997 |
| WO | 9815224 A2 | 4/1998 |
| WO | WO9857577 | 12/1998 |
| WO | WO9947039 | 9/1999 |
| WO | WO0059374 | 10/2000 |
| WO | WO0117421 | 3/2001 |
| WO | WO2005010567 | 2/2005 |

OTHER PUBLICATIONS

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

Weil, Max Harry, et al.; "Sublingual Capnometry: A New Noninvasive Measurement for Diagnosis and Quantitation of Severity of Circulatory Shock"; Cirtical Care Medicine, vol. 27, No. 7 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796.

Schulz, Christian Eric; "Design of a Pulse Oximetry Sensor Housing Assembly," California State University Master's Thesis, *UMI Dissertation Services*, UMI No. 1401306, (May 2000) 63 pages.

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary.

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Irie, A., et al.; "Respiration Monitors—Pulse Oximeters," *Neonatal Care*, vol. 15, No. 12, pp. 78-83 (2002) (Article in Japanese—contains English summary of article).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Urquhart, C., et al.; "Ear probe pulse oximeters and neonates," *Anaesthesia*, vol. 60, p. 294 (2005).

Bentley, David J. et al.; "Measure Pressure with Thin Film"; Paper Film & Foil Converter; May 1, 2003.
http://www.fcw.com.my/fujifilm.html.

International Search Report PCT/US2010/038105, 5 pages, mailed Oct. 21, 2010.

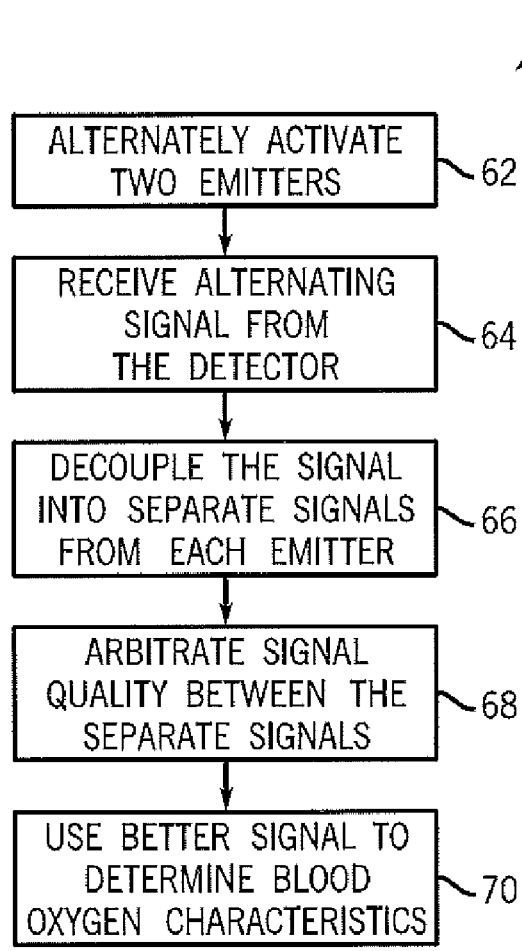
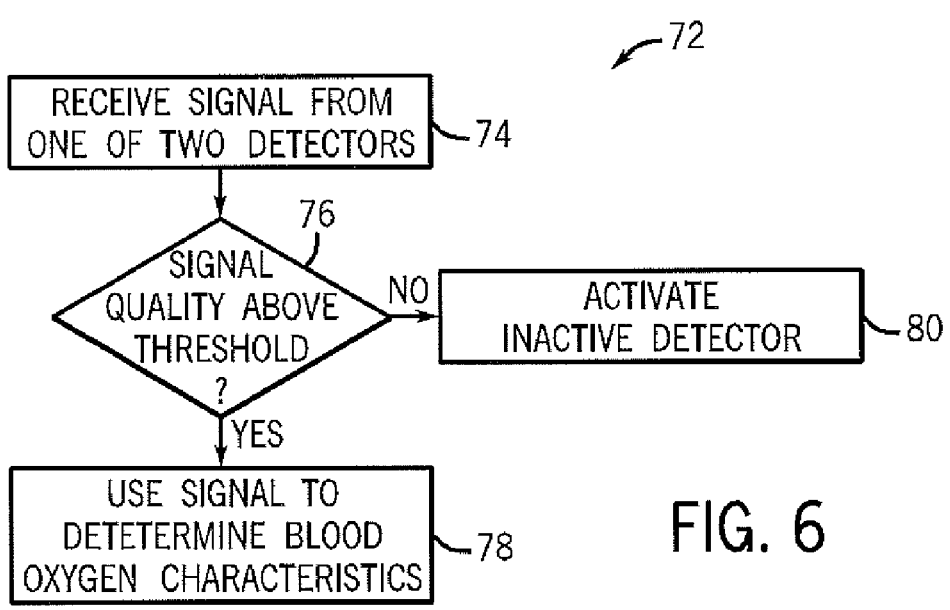

REFLECTANCE AND/OR TRANSMISSIVE PULSE OXIMETER

BACKGROUND

The present disclosure relates generally to medical devices and, more particularly, to sensors used for sensing physiological parameters of a patient.

This section is intended to introduce the reader to aspects of the art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed and/or scattered. More specifically, the light passed through the tissue is typically selected to be of one or more wavelengths that may be absorbed and/or scattered by the blood in an amount correlative to the amount of the blood constituent present in the blood. The amount of light absorbed and/or scattered may then be used to estimate the amount of blood constituent in the tissue using various algorithms.

Pulse oximetry sensors may be applied to a patient's tissue site and secured, for example by adhesives, clips, or light pressure, to achieve a conforming fit. Some outside light infiltration into the sensor may be avoided by fitting the sensor snugly against the patient's tissue. However, such a conforming fit may be difficult to achieve over a range of patient physiologies without adjustment or excessive attention on the part of medical personnel. Further, patient movement may also interfere with the signal received from the sensor. For example, for the case a bandage-type sensor wrapped around the fingertip, if the finger is bent at a first joint, parts of the sensor may fold or buckle away from the tissue. Such small changes in the conformation of the sensor may cause the optical components to lose their contact with the skin, resulting in changes to the emitted and/or detected light, which in turn may lead to signal artifacts. While these artifacts may sometimes be addressed by signal processing and filtering to mitigate the effects, such signal processing may be complex.

BRIEF DESCRIPTION OF THE DRAWINGS

Advantages of the disclosure may become apparent upon reading the following detailed description and upon reference to the drawings in which:

FIG. 5 is a flow diagram of a method of selecting between transmission mode or reflectance mode for a two detector sensor according to an embodiment;

FIG. 6 illustrates a pulse oximetry system coupled to a multi-parameter patient monitor and a sensor according to an embodiment;

DETAILED DESCRIPTION OF SPECIFIC EMBODIMENTS

Figure 1:
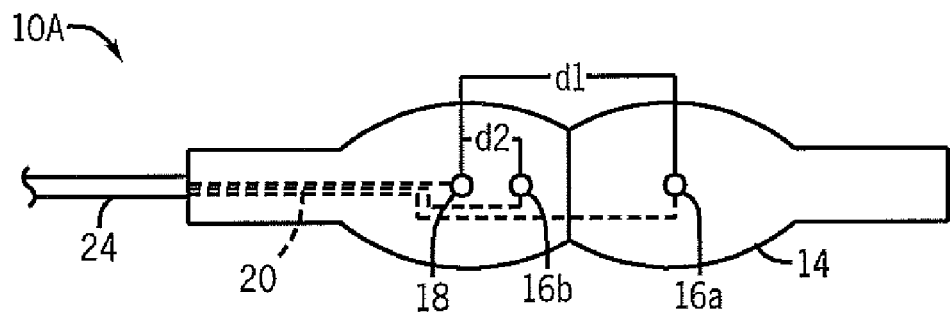
FIG. 1 is a perspective view of a dual-mode bandage-style sensor with two emitters according to an embodiment.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Medical sensors such as pulse oximetry sensors may be placed on a patient in a location that is normally perfused with arterial blood to facilitate measurement of the desired blood characteristics, such as arterial oxygen saturation measurement ($SpO_2$). For example, common sensor sites include a patient's fingertips, toes, earlobes, or forehead. In addition, pulse oximetry sensors may be capable of performing intrauterine measurements. Sensors in either reflectance-type or transmission-type configurations (or, in certain cases, transflectance-type configurations) may be able to sense light that has been transmitted through the tissue.

Sensors as provided herein may be able to operate in both "transmission mode" and "reflectance mode." Transmission mode sensors include an emitter and detector that are typically placed on opposing sides of the sensor site. If the sensor site is a fingertip, for example, the sensor assembly is positioned over the patient's fingertip such that the emitter and detector lie on either side of the patient's nail bed. In other words, the sensor assembly is positioned so that the emitter is located on the patient's fingernail and the detector is located approximately 180° opposite the emitter on the patient's finger pad. During operation, the emitter shines one or more wavelengths of light through the patient's fingertip and the light received by the detector is processed to determine various physiological characteristics of the patient. In each of the embodiments discussed herein, it should be understood that the locations of the emitter and the detector may be exchanged. For example, the detector may be located at the top of the finger and the emitter may be located underneath the finger. In either arrangement, the sensor assembly will perform in substantially the same manner.

Reflectance mode sensors also operate by emitting light into the tissue and detecting the light that is transmitted and/or scattered by the tissue. However, reflectance type sensors include an emitter and detector that are typically placed on the same side of the sensor site. For example, a reflectance type sensor may be placed on a patient's fingertip or forehead such that the emitter and detector lie side-by-side. Reflectance type sensors detect light photons that are scattered back to the detector. Sensor assemblies may also be "transflectance," such as a sensor that may subtend a portion of a baby's heel.

Regardless of the placement of a sensor used for pulse oximetry, the reliability of the pulse oximetry measurement is related to the accurate detection of transmitted light that has passed through the perfused tissue and that has not been supplemented by undesired light sources or that has not been scattered or redirected before passing through the tissue and being detected. In addition, the reliability of the measurements may be affected by appropriate calibration of the received sensor signals to account for properties of the sensor and/or the sensing components. For example, reflectance-type sensors may be calibrated to account for the distance between the emitter and the detector on the sensor, which may influence the path length of the detected light. Transmission-type sensors may be calibrated to account for an estimated path length that reflects the width of the intended measurement site, such as a finger or an ear lobe. Accordingly, because sensors may be specifically calibrated for transmission use versus reflectance use, the quality of a sensor's measurements may be degraded if a transmission-type sensor is inadvertently used in a reflectance-type configuration.

As disclosed herein, sensors for pulse oximetry or other applications utilizing spectrophotometry are provided that may be capable of being used in both reflectance mode and transmission mode. Such sensors may provide distinct advantages for healthcare practitioners. Upon a decrease in signal quality, such dual-mode sensors may switch from reflectance mode to transmission mode or vice versa to improve the measured signal quality. For example, when a patient wearing a digit sensor taps a finger on a hard surface, the resultant signal artifacts may influence the signal from a reflectance mode sensor more profoundly, particularly if both the emitter and the detector, which are side-by-side, are directly tapped against the surface. By switching to transmission mode and activating a different detector on the opposing side of the sensor, the influence of the tapping motion on the signal may be decreased because, while the original emitter may still be directly affected by the tapping, the different detector on the opposing side of the sensor may be relatively shielded from the tapping motion. Further, switching modes may allow practitioners to sample different areas of the tissue to determine if a particular mode offers increased signal quality. For example, relatively small areas of tissue discoloration or low perfusion may be avoided by sampling both transmission mode and reflectance mode signal quality and selecting the highest quality signal.

FIG. 1 illustrates an example of a dual-mode bandage-type sensor 10A appropriate for use on a patient's digit. The sensor body 14 includes a transmission mode emitter 16a/detector 18 pair disposed on its surface. In addition, the sensor 10A also includes a second emitter 16b, which may pair with detector 18 in a reflectance mode arrangement. The sensor body 14 may include suitable electrical connectors, such as wire leads 20, that may operatively connect the emitters 16a and 16b and the detector 18 to a cable 24, which may be connected to a downstream monitoring device. The sensor 10A may also include an adhesive layer (not shown) in order to enhance the sensor's fit to the tissue.

The emitter 16a and detector 18 may be spaced apart on the sensor body 14 any suitable distance $d_1$ for a transmission-type arrangement. For example, the appropriate spacing $d_1$ may be 20-25 mm apart. In addition, the emitter 16b and the detector 18 may be spaced apart any suitable distance $d_2$ for a reflectance-type arrangement. In one embodiment, the distance $d_2$ may be 8-14 mm. As shown, emitter 16b is disposed between 16a and 18. However, it should be understood that emitter 16b may be located anywhere on the sensor body 14 such that the distance $d_2$ and configuration (e.g., the spacing and placement on the tissue) between 16b and 18 is appropriate for reflectance mode measurements.

Figure 2A:
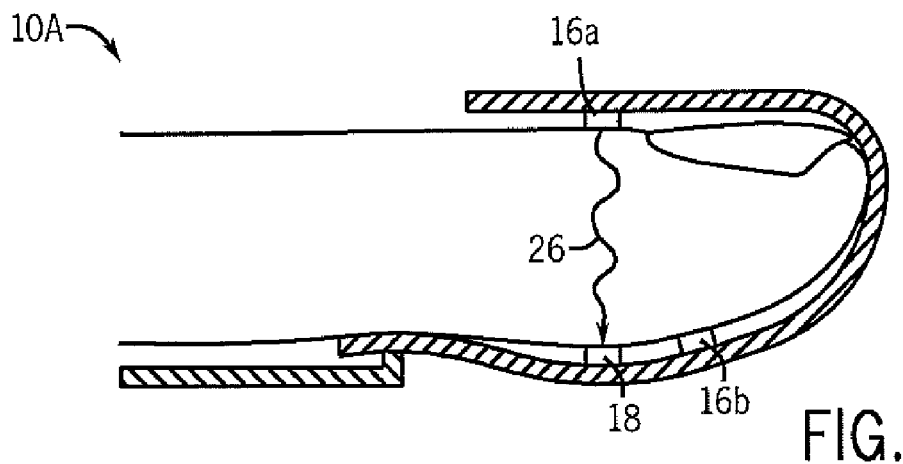
FIG. 2A is a side view of the sensor of FIG. 1 applied to a patient's digit and operating in transmission mode according to an embodiment.
Figure 2B:
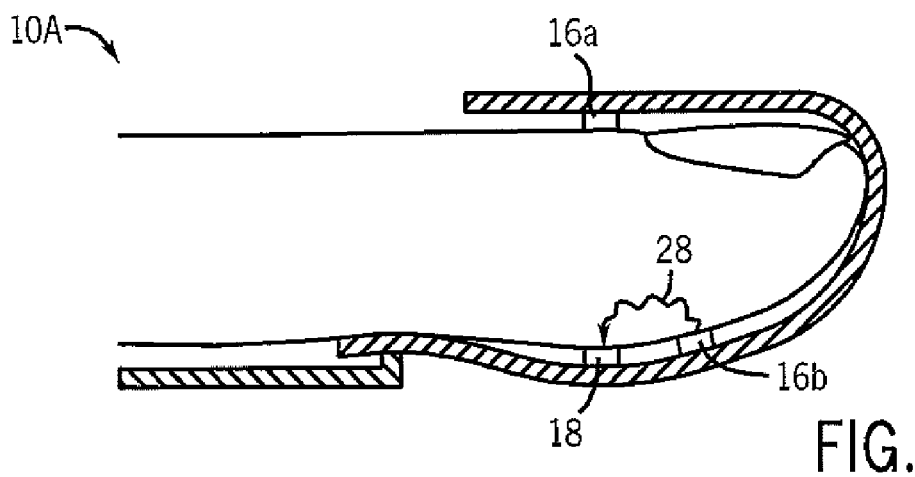
FIG. 2B is a side view of the sensor of FIG. 1 applied to a patient's digit and operating in reflectance mode according to an embodiment.

FIGS. 2A and 2B depict the sensor 10A applied to a patient's digit. FIG. 2A is a side view of sensor 10A operating in transmission mode, during which emitter 16a is active and emitter 16b is inactive. The light, depicted by arrow 26, emitted by emitter 16a travels through the tissue and is detected by detector 18. In FIG. 2B, the sensor 10A is shown operating in reflectance mode. In reflectance mode, a monitor or other device activates emitter 16b and not emitter 16a. The light 28 from emitter 16b is detected by the detector 18. As shown, the emitter 16b and the detector 18 may be arranged to be secured to the palmar side of the digit. Alternatively, the sensor 10A may be applied to the digit such that the emitter 16b and the detector 18 are secured to the nail side of the digit and the emitter 16a is applied on the palmar side.

Figure 3:
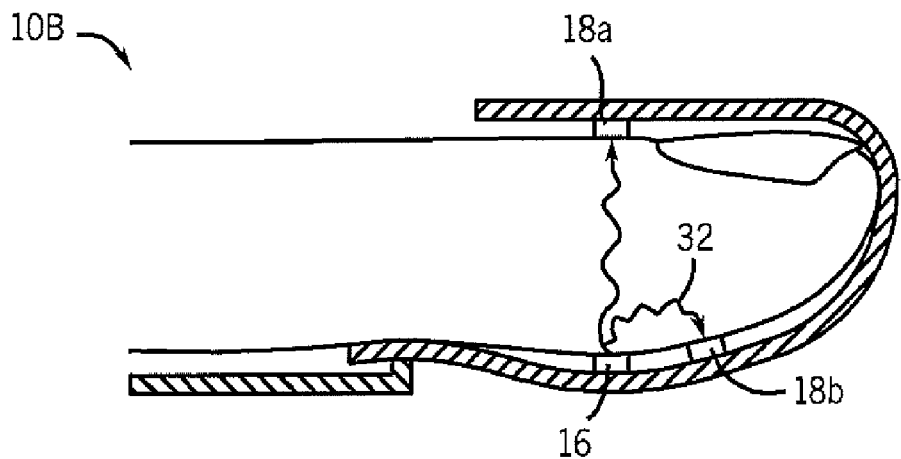
FIG. 3 is a side view of a dual-mode sensor with two detectors operating in reflectance mode and transmission mode simultaneously according to an embodiment.

In an alternative arrangement, a sensor may include multiple detectors 18 and a single emitter 16. As shown in FIG. 3, a sensor 10B may include an emitter 16 and detector 18a that are configured to operate in transmission mode in which light 30 from the emitter 16 travels through the tissue and encounters detector 18a. A second detector 18b may be configured to pair with emitter 16 in reflectance mode and detect light 32. As shown, the transmission and reflectance modes may operate simultaneously. In other embodiments, the detectors 18a and 18b may be activated at different times.

As noted above, sensors 10 as provided herein may include one or more emitters paired with a single detector or one or more detectors paired with a single emitter. Regardless of the configuration of the optical sensing components, such sensors 10 may be able to switch between reflectance and transmission modes or, in embodiments, operate both modes simultaneously. As such, an upstream medical device may receive one signal from each emitter-detector pair or each "mode." These signals may be further processed to determine if a particular mode provides higher signal quality or is associated with fewer signal artifacts.

Figure 4:
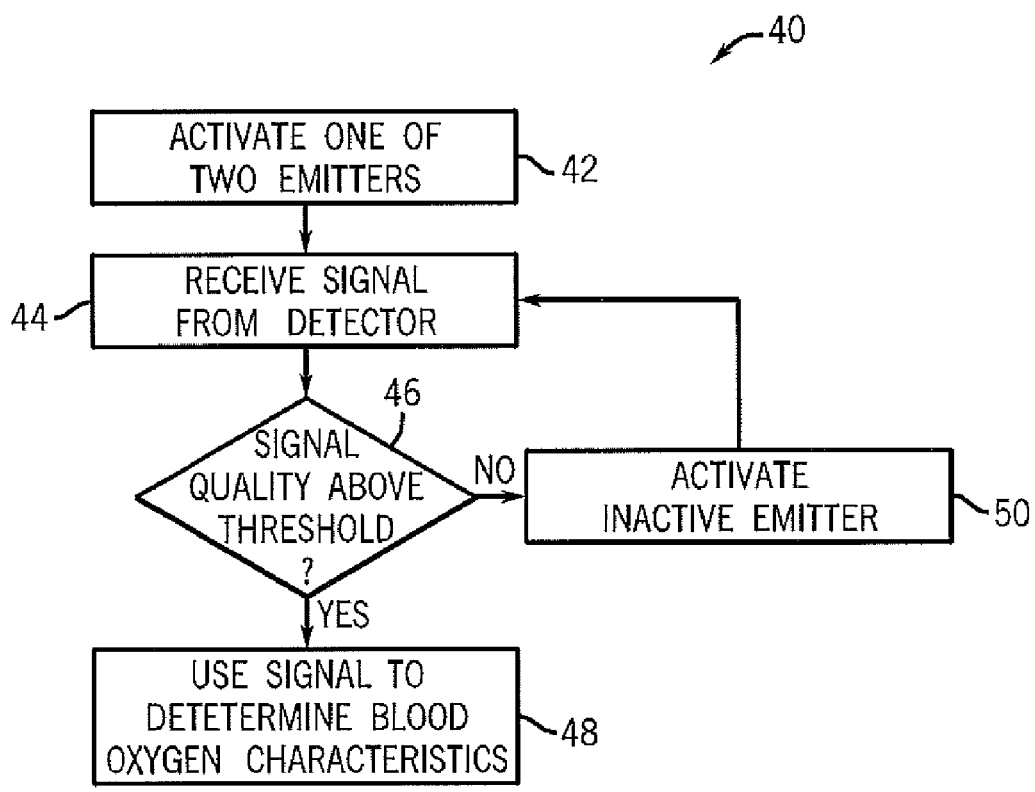
FIG. 4 is a flow diagram of a method of selecting between transmission mode or reflectance mode for a two emitter sensor according to an embodiment.

FIG. 4 is a flow diagram of a method 40 for processing sensor signals from both transmission and reflectance modes that may be used in conjunction with a sensor including multiple emitters, such as sensor 10A. At step 42, one of the two emitters 16 is activated, i.e., a drive signal is provided to the emitter from an upstream device. For certain types of sensors 10, a sensor may start out in a default mode, for example a transmission mode may be the default setting and the emitter 16a may be activated while emitter 16b is inactive. For other types of sensors 10, an operator may manually select a starting mode for operation, which may depend on the tissue site to be measured or other patient factors. At step 44, the signal from the detector 18 is received, for example by the upstream device, for processing. At step 46, any suitable processing method for determining signal quality may be employed to assess the quality of the received signal and to determine if the signal has attained a certain minimum threshold quality. In one embodiment, the signal quality may be assessed by performing a pulse qualification on the signal. In other embodiments, the signal quality may be assessed by determining a ratio of ratios for the signal. Such signal quality assessments may be performed as provided in U.S. Pat. No. 7,209,774, the specification of which is incorporated by reference herein in its entirety herein for all purposes. Other methods for determining signal quality may include detecting characteristic artifacts associated with certain types of patient or sensor movement.

If the signal of the default mode is determined to be of sufficient quality, the signal may then be used at step 48 to determine blood oxygen characteristics (or other physiological parameters), such as pulse rate and blood oxygen saturation. However, if the signal quality falls below a certain threshold, the inactive emitter 16, representing the "non-default" mode, may be activated at step 50. The signal from this emitter 16 may be received at step 46 and evaluated at step 48 for signal quality. If the signal quality from step 50 is above the threshold, then the sensor will continue to operate in the higher quality mode. If the signal quality from step 50 also falls below the quality threshold, then the device may prompt various alerts or error messages. The process 40 may be repeated to continuously or periodically assess the signal quality of the mode in use.

While the above method 40 may allow for switching modes between transmission and reflectance (or vice versa) only when an active mode falls below a certain quality, a sensor 10A may also provide alternating signals from both modes to an upstream device that may be continually arbitrated to determine the best quality signal, which may then be used to calculate blood oxygen characteristics. FIG. 5 is a flow diagram of a method 60 that may be used in conjunction with a sensor with two emitters, such as sensor 10A. At step 62, emitters 16a and 16b are alternately activated, such that when one is active, the other is inactive. The alternate activation may be one the order of microseconds or seconds and may be accomplished by a light drive input signal from a medical device as well as additional inputs or controls located on the sensor 10A and/or on the device, as discussed below (see FIGS. 10 and 11). The upstream medical device may receive the alternating signal (i.e., a signal that includes information from both emitters 16a and 16b) from the detector 18 at step 64. At step 66, the signals may be decoupled into separate signals from each emitter 16a and 16b, for example using timing information from a light drive and time processing unit. Alternatively, the signals may be decoupled using intensity information. For example, transmission mode signals may be generally about half the amplitude of reflectance mode signals because of the greater distance between the transmission mode emitter-detector pair.

Regardless of how the signals from each emitter 16 are separated, the separated signals may then be further processed at step 68 to determine signal quality. As discussed above, signal quality metrics may be measures of artifact contribution, pulse qualification or of a ratio-of-ratios calculation. The higher quality signal may be used in step 70 to determine blood oxygen characteristics. The signals from each emitter 16 may be continuously arbitrated such that the higher quality signal within a predetermined time window may be used.

As noted above, in addition to sensor configurations with two emitters, sensors may include a single emitter 16 and two detectors 18 that may form both transmission-type and reflectance-type emitter-detector pairs. FIG. 6 is a flow diagram of a method 72 that may be used in conjunction with a sensor 10B. At step 74, one of the two detectors 18 is activated, i.e., the incoming signal is received and accessed for further processing at an upstream medical device. The sensor 10B may start out in a default mode, for example a transmission mode may be the default setting and the detector 18a may be activated while detector 18b is inactive, or the default mode may be input by an operator. At step 76, any suitable processing method for determining signal quality may be employed to assess the quality of the received signal from the active detector 18 and to determine if the signal has attained a certain minimum threshold quality. If the signal of the default mode is determined to be of sufficient quality, the signal may then be used at step 78 to determine blood oxygen characteristics. However, if the signal quality falls below a certain threshold, the inactive detector 18, representing the "non-default" mode, may be activated at step 80, and the signal from this detector may be further processed to determine its signal quality.

Figure 7:
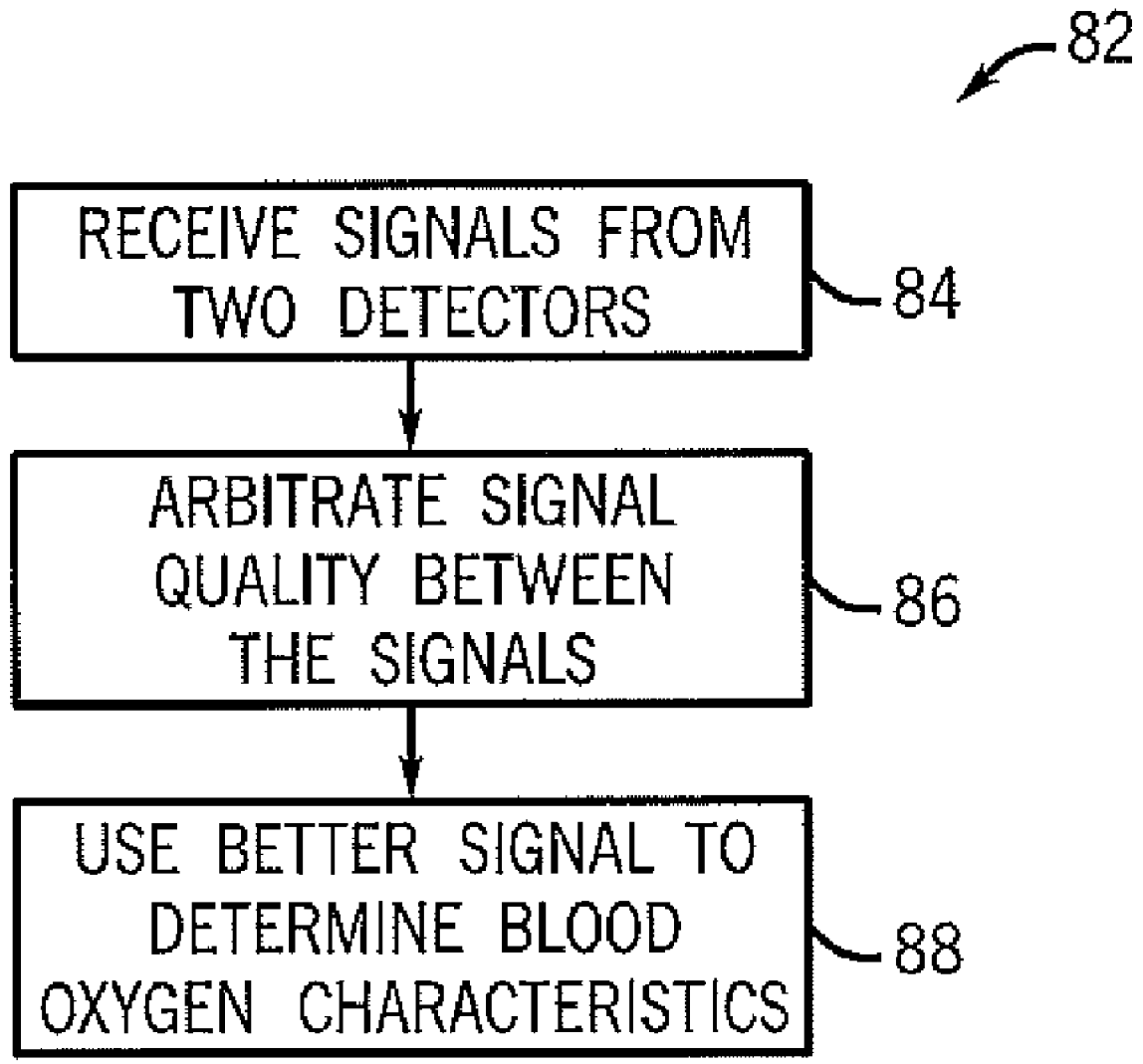
FIG. 7 is a block diagram of a pulse oximetry system according to an embodiment.

In one embodiment, a sensor 10B may operate transmission mode and reflectance mode simultaneously (see FIG. 3). In such an embodiment, detectors 18a and 18b may receive light concurrently from emitter 16. FIG. 7 is a flow diagram of a method 82 that may be used in conjunction with a sensor 10B during either simultaneous operation of both detectors 18a and 18b or, in embodiments, alternate operation of both detectors 18. At step 84, incoming signals from detectors 18a and 18b are received and accessed for further processing at an upstream medical device. Signal quality of both detector signals may be assessed by any suitable method at step 86 and the signal quality may be arbitrated. At step 88, the higher quality signal may be used to determine blood oxygen characteristics.

Figure 8:
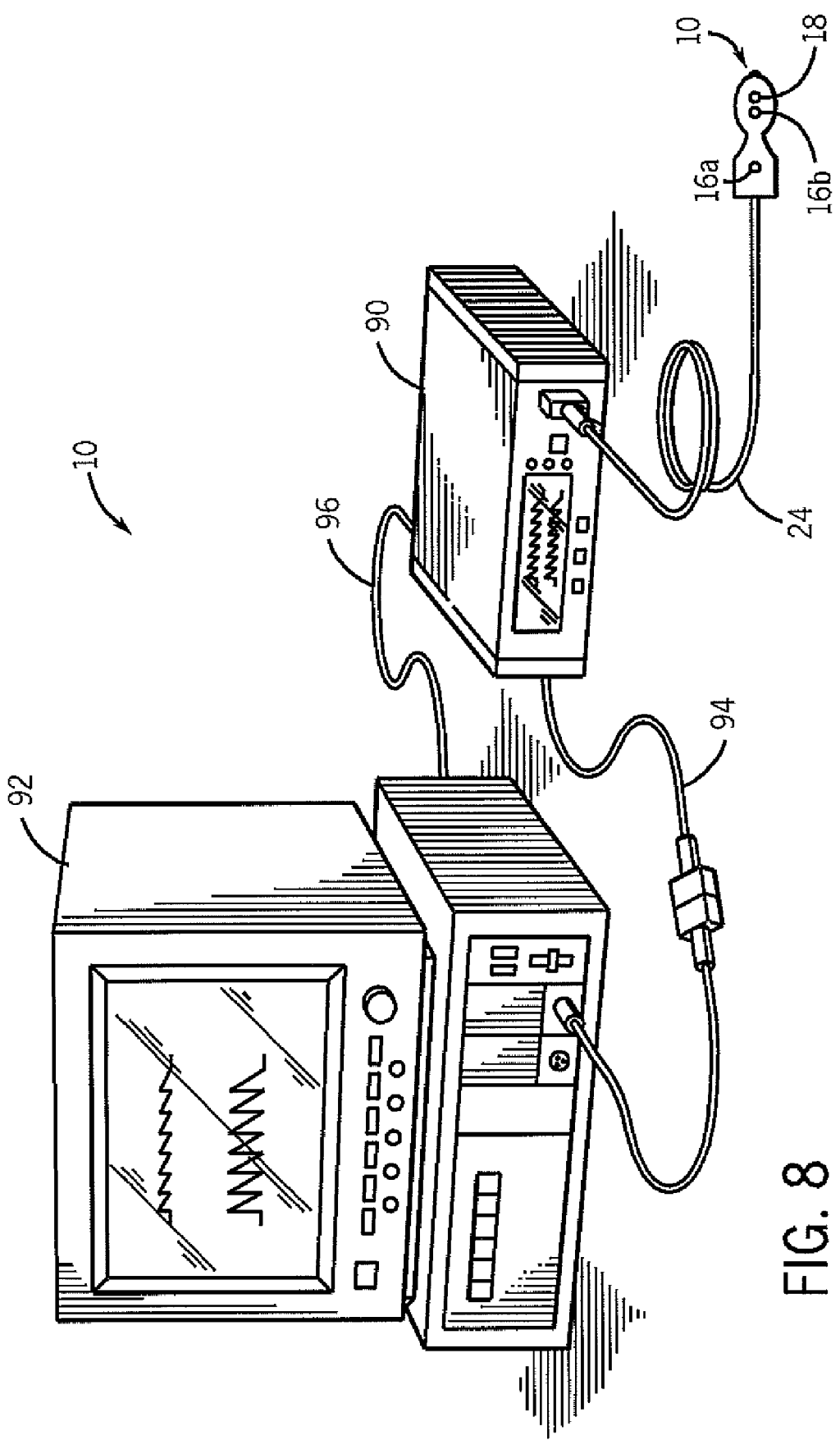
FIG. 8 is a block diagram of a dual-mode sensor with two emitters and a control on the monitor for switching between the two emitters according to an embodiment.

A sensor or sensor assembly, illustrated generically as a sensor assembly 10, may be used in conjunction with a pulse oximetry monitor 90, as illustrated in FIG. 8. It should be appreciated that the cable 24 of the sensor assembly 10 may be coupled to the monitor 90 or it may be coupled to a transmission device to facilitate wireless transmission between the sensor assembly 10 and the monitor 90. The monitor 90 may be any suitable pulse oximeter, such as those available from Nellcor Puritan Bennett LLC. Furthermore, to upgrade conventional pulse oximetry provided by the monitor 90 to provide additional functions, the monitor 90 may be coupled to a multi-parameter patient monitor 92 via a cable 94 connected to a sensor input port or via a cable 96 connected to a digital communication port.

Figure 9:
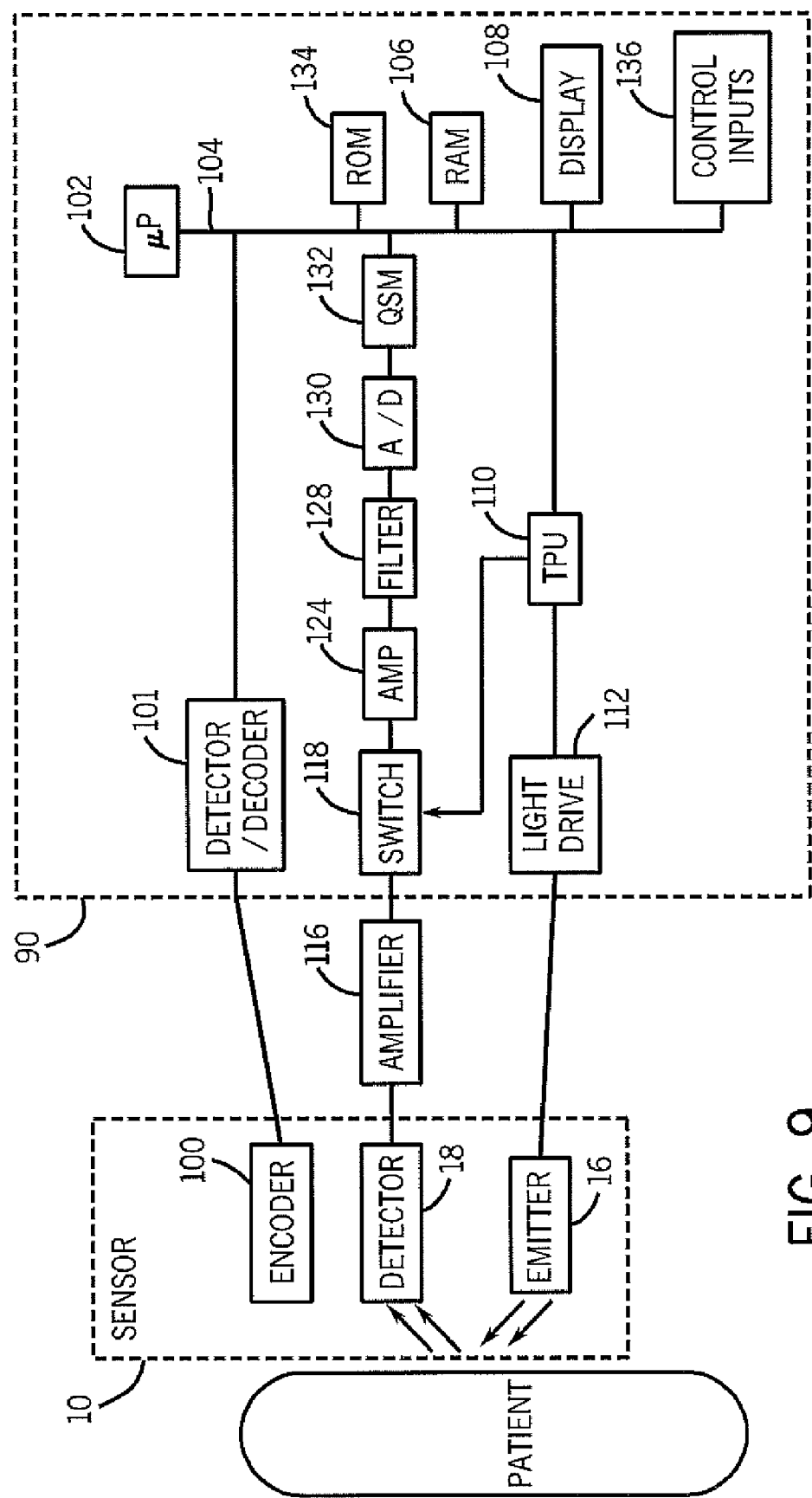
FIG. 9 is a block diagram of a dual-mode sensor with two emitters and a control on the sensor for switching between the two emitters according to an embodiment.

FIG. 9 is a block diagram of an embodiment of a pulse oximeter 90 that may be configured to implement the embodiments of the present disclosure. Light from one or more emitters 16 may pass into a blood perfused tissue, and may be scattered, and then detected by one or more detectors 18 An example of a sensor assembly 10 containing at least one emitter 16 and at least one detector 18 may also contain an encoder 100 which may be capable of providing signals indicative of the wavelength(s) of light source 16 to allow the oximeter to select appropriate calibration coefficients for calculating oxygen saturation. The encoder 100 may, in an embodiment, be a resistor.

In an embodiment, the sensor assembly 10 may be connected to a pulse oximetry monitor 90. The monitor 90 may include a microprocessor 102 coupled to an internal bus 104. Also connected to the bus may be a RAM memory 106 and a display 108. A time processing unit (TPU) 110 may provide timing control signals to light drive circuitry 112, which controls when the emitter 16 is activated, and if multiple light sources are used, the multiplexed timing for the different light sources. TPU 114 may also control the gating-in of signals from detector 18 through an amplifier 116 and a switching circuit 118. These signals are sampled at the proper time, depending at least in part upon which of multiple light sources is activated, if multiple light sources are used. The received signal from the detector 18 may be passed through an amplifier 124, a low pass filter 128, and an analog-to-digital converter 130. The digital data may then be stored in a queued serial module (QSM) 132, for later downloading to RAM 106 or ROM 134 as QSM 132 fills up.

In an embodiment, based at least in part upon the received signals corresponding to the light received by detector 18, microprocessor 102 may calculate the oxygen saturation using various algorithms. These algorithms may require coefficients, which may be empirically determined, and may correspond to the wavelengths of light used. The algorithms may be stored in a ROM 134 and accessed and operated according to microprocessor 102 instructions. For example, the encoder 100 may communicate with decoder 101 to allow the microprocessor 102 to determine the appropriate coefficients.

In an embodiment of a two-wavelength system, the particular set of coefficients chosen for any pair of wavelength spectra may be determined by a value indicated by the encoder 100 corresponding to a particular light source and particular emitter-detector separation distances in a particular sensor assembly 10. In one embodiment, multiple resistor values may be assigned to select different sets of coefficients, or the sets of coefficients may be stored on a digital medium. In another embodiment, the resistors are used to select from among the coefficients appropriate for an infrared source paired with either a near red source or far red source. The selection between whether the near red or far red set will be chosen can be selected with a control input from control inputs 136. Control inputs 136 may be, for instance, a switch on the pulse oximeter, a keyboard, or a port providing instructions from a remote host computer. Furthermore, any number of methods or algorithms may be used to determine a patient's pulse rate, oxygen saturation or any other desired physiological parameter.

The sensor assembly 10 includes at least one emitter 16 and at least one detector 18 that may be of any suitable type. For example, the emitter 16 may be one or more light emitting diodes adapted to transmit one or more wavelengths of light in the red to infrared range, and the detector 18 may one or more photodetectors selected to receive light in the range or ranges emitted from the emitter 16. Alternatively, an emitter 16 may also be a laser diode or a vertical cavity surface emitting laser (VCSEL). An emitter 16 and detector 18 may also include optical fiber sensing elements. An emitter 16 may include a broadband or "white light" source, in which case the detector could include any of a variety of elements for selecting specific wavelengths, such as reflective or refractive elements or interferometers. These kinds of emitters and/or detectors would typically be coupled to the rigid or rigidified sensor via fiber optics. Alternatively, a sensor assembly 10 may sense light detected from the tissue is at a different wavelength from the light emitted into the tissue. Such sensors may be adapted to sense fluorescence, phosphorescence, Raman scattering, Rayleigh scattering and multi-photon events or photoacoustic effects.

For pulse oximetry applications, the oxygen saturation of the patient's arterial blood may be determined using two or more wavelengths of light, most commonly red and near infrared wavelengths. Similarly, in other applications, a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra.

The emitter 16 and the detector 18 may be disposed on a sensor body, which may be made of any suitable material, such as plastic, foam, woven material, or paper. Alternatively, the emitter 16 and the detector 18 may be remotely located and optically coupled to the sensor assembly 10 using optical fibers. In the depicted embodiments, the sensor assembly 10 is coupled to a cable 24 that is responsible for transmitting electrical and/or optical signals to and from the emitter 16 and detector 18 of the sensor assembly 10. The cable may be permanently coupled to the sensor assembly 10, or it may be removably coupled to the sensor assembly 10—the latter alternative being more useful and cost efficient in situations where the sensor assembly 10 is disposable.

Figure 10:
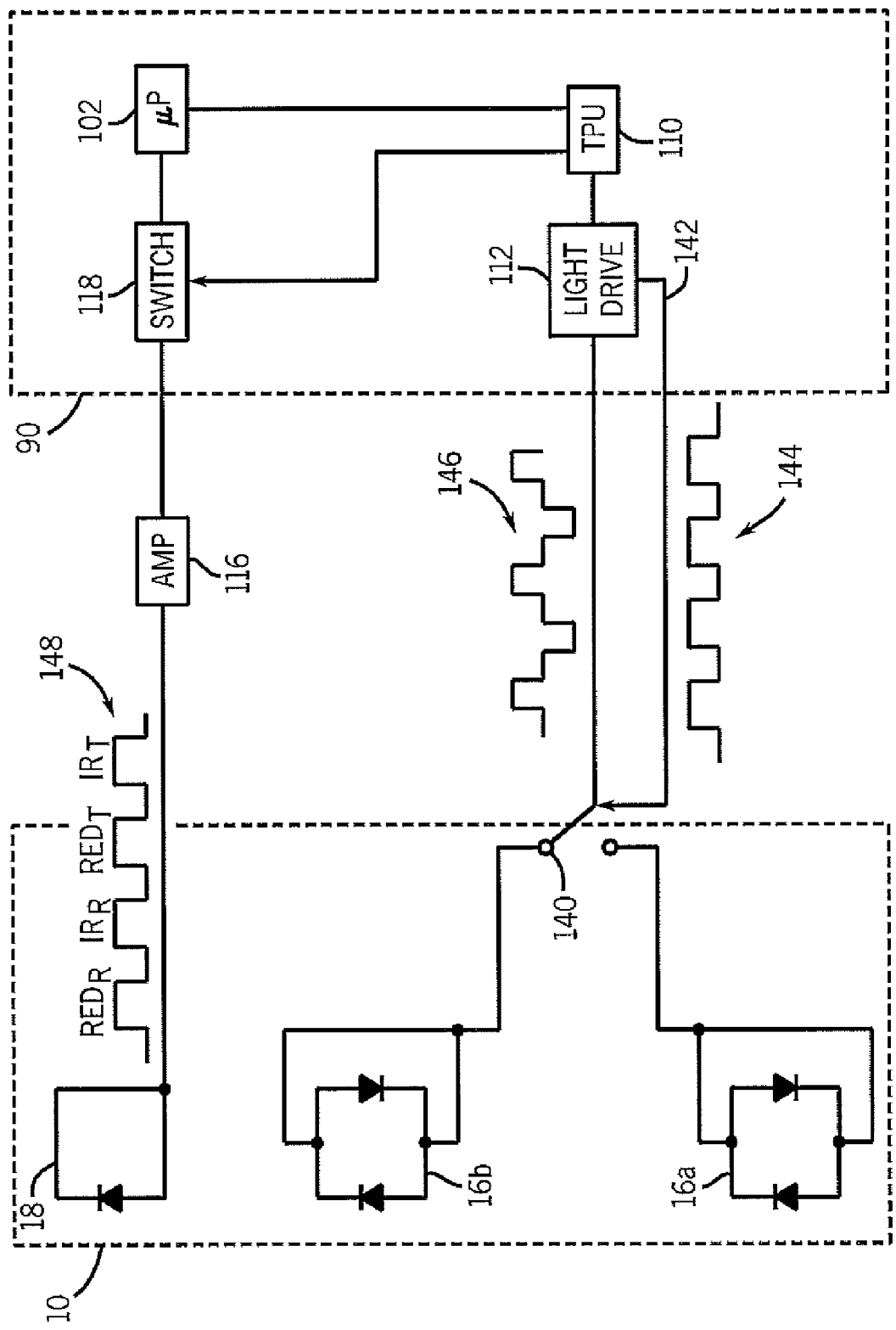
FIG. 10 is a block diagram of a dual-mode sensor with two emitters and a control on the monitor for activating each emitter according to an embodiment.

Depending on the particular configuration of the sensor 10, the sensor 10 and/or the monitor 90 may include certain devices for controlling the activation of either two separate emitters 16 or two separate detectors 18. As shown in FIG. 10, a monitor 90 may provide an input signal 142 to a switch 140 that controls switching between emitter 16a and emitter 16b. As shown, switch 140 may be a hardware switch located on the sensor 10. In other embodiments, the switch 140 may be associated with cable 20 or may be located in the monitor 90. The input signal 142 may be generated by light drive 112 and, as shown, may be an alternating signal 144 that causes the sensor 10 to periodically switch between emitter 16a and emitter 16b. It should be understood that the shape of signal 144 may be changed as desired or according to various inputs from microprocessor 102 (e.g., signal quality inputs) to provide different activation times for each emitter 16. For example, the signal 144 may activate only emitter 16a or only emitter 16b until signal quality from the active emitter 16 deteriorates. Light drive 112 may also generate a drive signal 146 to alternately drive a red and IR photodiode pair for the active emitter 16. The detector signal 148 includes both the red and IR components from the active emitter 16. When emitter 16a and emitter 16b are alternately activated, the detector signal 148 received at switch 118 may include a $Red_R$ portion (red reflectance), an $IR_R$ portion (IR reflectance), a $Red_T$ portion (red transmission) and an $IR_T$ portion (IR transmission). Input from the time processing unit 110 may be used to assign parts of the signal to the appropriate emitter-detector pair (e.g., reflectance or transmission).

Figure 11:
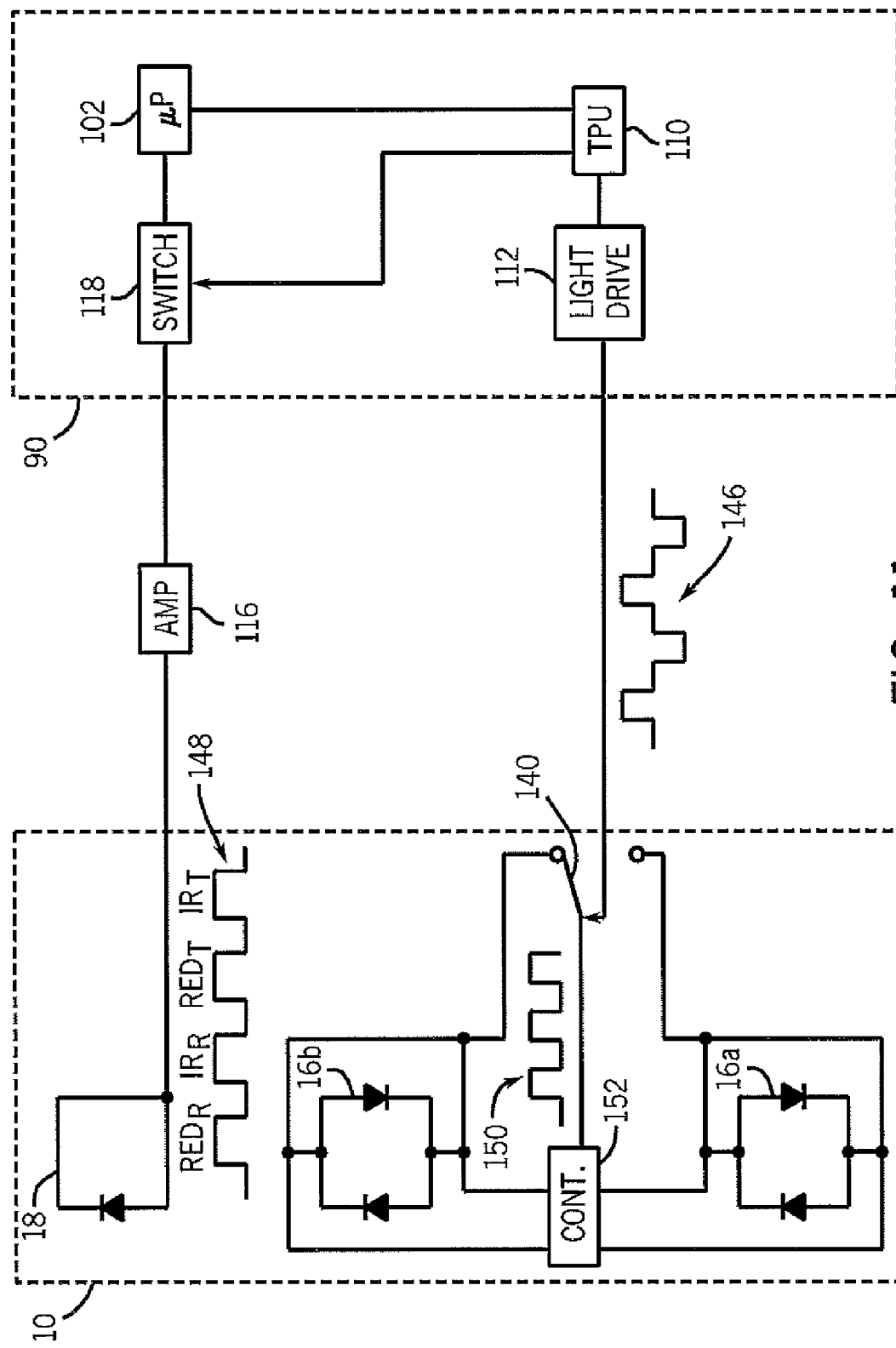
FIG. 11 is a block diagram of a dual-mode sensor with two emitters and a control on the sensor for activating each emitter according to an embodiment.

In an alternate configuration, shown in FIG. 11, an input signal 152 to the switch 140 may be controlled by a controller 152, which may be located on the sensor 10. Controller 152 may receive inputs from emitter 16a and emitter 16b. Regardless of whether the control for the switch 140 is generated by the monitor 90 or the sensor 10, the red and IR diodes on each emitter 16 may further be controlled by light drive 112 and drive signal 146. The detector signal 148 includes both the red and IR components from the active emitter 16. In such a configuration, the sensor 10 may be adapted to work with off-the-shelf monitors 90, which may not need to include addition hardware or software instructions for controlling the switch between emitters 16a and 16b.

Figure 12:
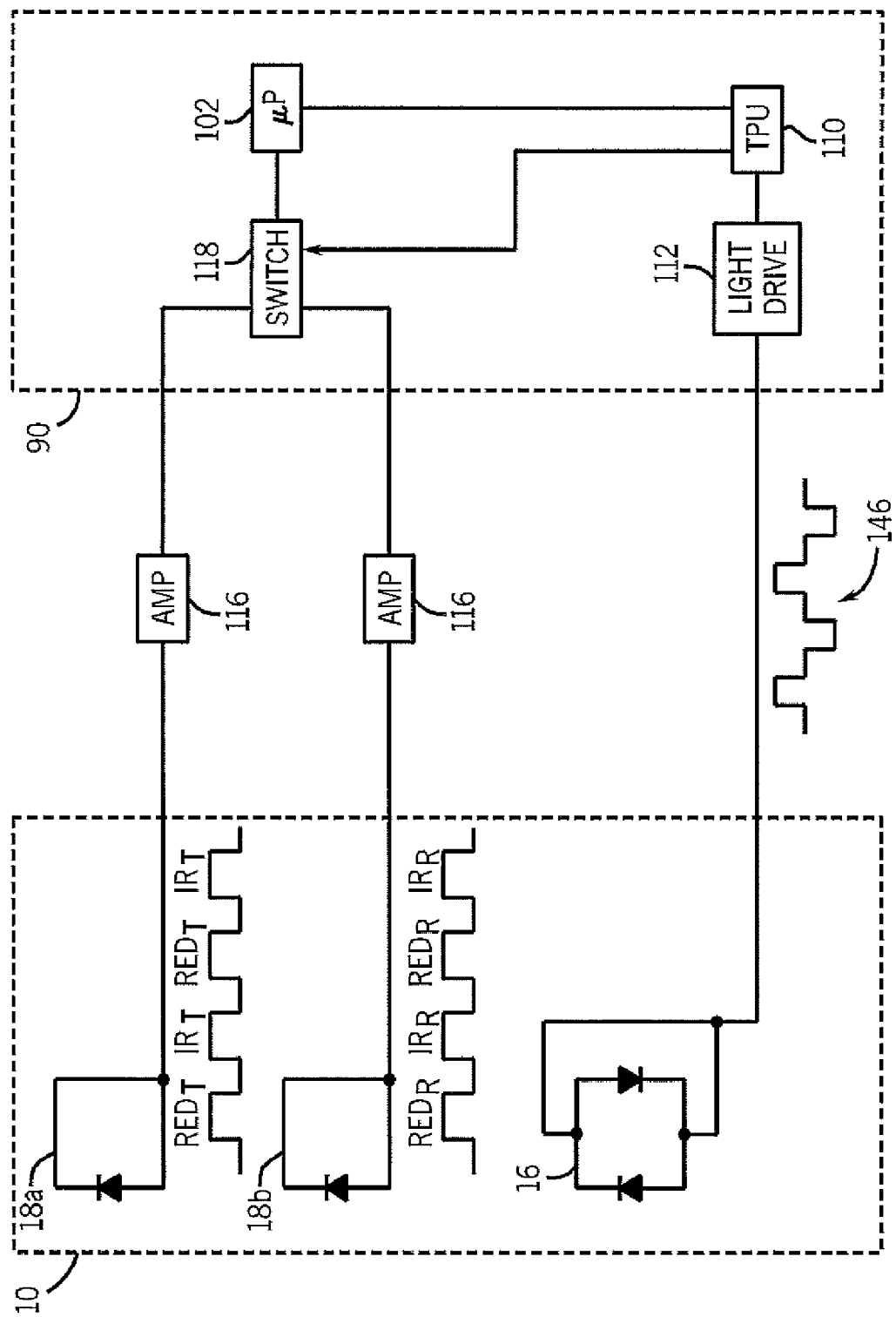
FIG. 12 is a block diagram of a dual-mode sensor with two detectors according to an embodiment.

For sensor configurations in which two detectors 18 are employed, the signals from each detector 18a and 18b may be processed within the monitor 90. As shown in FIG. 12, light drive 112 may drive a single emitter 16 with drive signal 146. When the light from the emitter 16 impinges the detectors 18a and 18b, the detector 18a generates a transmission mode signal 160 that includes alternating $Red_T$ portions and $IR_T$ portions while the detector 18b generates a reflectance mode signal that includes alternating $Red_R$ portions and $IR_R$ portions. These signals may be passes through one or more amplifiers 116 and received at switch 118 for further processing by microprocessor 102. For embodiments in which the signal from one detector 18 is to be disregarded or considered inactive, for example when a particular mode is associated with low signal quality, the monitor 90 may not use the received signal from the inactive time window. Time processing unit 110 may provide time stamps to the received signals to determine the inactive and active time windows for each detector 18.

Microprocessor 102 may employ various algorithms and signal processing methods to detect and/or mitigate various types of signal artifacts associated with one or more emitter-detector pairs from transmission mode and/or reflectance mode measurements. Such signal artifacts may be the result of periodic and aperiodic movement of the sensor or sensor site within the frequency band pass of the monitor 90, which may cause time-varying photocurrents that may obscure, corrupt, or overwhelm the arterial blood pulsations. Certain types of signal processing techniques may be employed to overcome certain types of signal artifacts, which may one or more of (1) η-artifacts, (2) α-artifacts, (3) $\Delta P_{tiss}$-artifact, (4) heterogeneity artifacts, and (5) boundary condition artifacts. In addition, when such signal artifacts are detected, the sensor 10 may automatically switch from the active mode (e.g., transmission or reflectance) to the inactive mode to determine if the signal artifact effects are mitigated by the switch.

1. η-Artifacts

The η-artifacts (light coupling efficiency variations with time) may be related to a variation in light amplitude as a result of sensor movement relative to the tissue, the amount of light that reaches the skin, or the amount of light that strikes the photodetector. There may or may not be symmetry in the amount of the artifact between IR and red signals, depending on the source of the variation. In one embodiment, the artifact may be at least in part the result of Fresnel coupling changes, which may be related to variations in the index of refraction of the emitter, the skin, any air gap between the sensor and the sensor site, and any adhesive used. Further, as the emitter 16 and detector 18 move relative to the surface of the skin, these air gaps may open, close, or otherwise change. The resulting "Fresnel variations" in the light coupling may be as large as or larger than the magnitude of the plethysmographic signal.

Accordingly, switching or arbitrating between transmission and reflectance modes may mitigate some effects of geometric changes to the sensor 10 because not all movements affect the sensor geometry symmetrically. Certain types of movements may result in larger artifacts for one mode versus another. For example, an air gap between a sensor surface and a tissue site may be localized around the transmission emitter 16a and may have less of an effect on the reflectance emitter 16b.

In addition to Fresnel coupling variations, z-axis variation may be the result of changes in the geometry of the emitter 16 relative to the skin, which may result in some of the light shunting around the skin and bouncing off of another surface. The total power of the light emitted into the tissue bed may vary with the geometry of the emitter 16. Further, the geometry of the detector may also result in similar variation.

As the physical separation between the emitter 16 and the detector 18 changes, the amount of light captured by the detector varies. This is due, in part, to the varying amount of tissue the light traverses. In general, the farther apart the spacing, the less light detected. Thus, modulating the emitter-detector spacing may result in signal artifacts. In sensors 10 as provided, a switch to transmission mode, in which the spacing is farther apart, from reflectance mode, in which the spacing is relatively closer, may mitigate the effects of such modulation. In transmission mode, because the emitter and detector are farther apart, any change in distance may be a smaller percentage of the emitter-detector spacing, thus the artifact may be a smaller contribution to the signal. However, depending on the type of movement, reflectance mode configurations may have improved signal quality because of relatively higher signal amplitude. Further, anti-η-artifacts may result when the emitter tilts on the red-IR axis such that the varying emitter-to-skin spacing is not equal for both of the emitter pairs (e.g., the red LED and the IR LED for a light emitting diode pair). This may result in as much as a 180° phase shift of the red and IR plethysmographic signals if the tilting is asymmetric.

2. α-Artifacts

The α-artifacts (e.g., blood sloshing) may be related to variation in blood flow 20 dynamics. When subjected to acceleration or a change in acceleration, the blood in the tissue will tend to resist this change due to its mass and will move to the down-hill side of the tissue. Since the degree of light absorption within the tissue bed is a function of the amount of absorber present, the shifting blood volume results in changes in the detected light level. Venous blood dominates these changes, but is not solely responsible. Such changes may occur independently of sensor adhesion factors. For example, moving a digit up and down may cause blood volume changes related to gravity. When the movement stops, there may be a time delay (e.g., the "blood slosh" settling back into position) associated with establishing a new DC level. Instead of waiting for the signal to settle into a new DC level, these types of artifacts may be mitigated by switching modes during the time delay.

3. $\Delta P_{tiss}$-Artifacts

The $\Delta P_{tiss}$-artifacts (e.g., changes in applied forces) may be the result of pressure applied to the tissue that results in localized blood redistribution to neighboring regions where the pressure is lower. Pressing or bending the tissue may result in movement of blood, movement of subcutaneous structures, changes in relative position of subcutaneous structures, changes in scattering properties of compressible portions of the tissue, changes in coupling efficiency (e.g., Fresnel coupling changes), and a varying degree of shunting. Thus, pressing on or near the sensor 10 may result in changes to the detected light levels. Also include in this category of artifacts may be the effect of sensor deformation caused by the pressure changes. For example, bending a digit at the joint may cause changes in skin color, which are related to local pressure changes. Further, such changes in tissue shape may also influence shunting that occurs at the level below the epidermis. Such changes may effect certain areas of the tissue more profoundly. For example, bending at a joint may cause localized exsanguination on the palmar side of the digit while causing an increase in redness on the side of the digit. Depending on the location of various emitters 16 and detectors 18 associated with transmission mode or reflectance mode, switching modes during a bending, pressing, or flexing motion may provide a higher quality signal.

4. Heterogeneity Artifacts

In both reflectance and transmission sensor geometries, the probing light passes through several types of tissues, depending on where the sensor is located: dermis, fat, muscle, tendon, bone, vessels, etc. Each of these different tissues uniquely affect the way in which light passes, as they each have their own scattering and absorbing properties. If movement of the sensor sites causes these structures to move relative to the sensor, the detected light levels will change. Absorption and scattering properties are wavelength dependent, thus the magnitude of these changes will not be the same in the red and IR channels. Such heterogeneity artifacts may include xy-axis sensor movement (movement of the sensor that causes the light to strike different areas of the tissue) and subcutaneous object motion (moving vessels and subcutaneous structures will modulate the light signals and may corrupt the plethysmographic signal. For sensors 10 as provided, switching modes may provide a sampling of signal quality through multiple paths. For certain patients, a particular mode may provide an optical path that is less subject to heterogeneity artifacts. For example, reflectance mode may involve an optical path that travels through fewer subcutaneous structures. Because these effects vary from patient to patient, arbitrating the signal quality between the modes at the time of application of the sensor 10 may allow the higher signal quality mode to be used.

5. Boundary Condition Artifacts

Boundary condition artifacts may encompass changes in light losses due to changes in shape of the finite boundaries of the tissue site. As the tissue bends, the surfaces may compress, stretch, fold, etc. Detected light that has travelled close to the surface will become more or less strongly attenuated as the surface geometry affects how much scatters out of the tissue. If a reflective surface is nearby, some of the light may be returned to the tissue and may or may not contribute to the overall signal, depending on where the light reenters the tissue. Secondary light modulation may occur when light exits the tissue outside of the aperture of the detector 18. Some of this light may be reflected back into the tissue to eventually reach the detector 18. If the efficiency of this process changes as a result of other artifacts, this may also influence the quality of the signal. Accordingly, switching to a second detector (e.g., detector 18b) on a different area of the tissue may provide improved signal quality when a primary detector is experiencing boundary condition artifacts.

The below tables summarize the contribution of various types of motions to a particular type of artifact. Table 1 shows the artifact effects for a transmission-type digit sensor, Table 2 shows the artifact effects for a reflectance-type forehead sensor, and Table 3 shows the artifact effects for a STORM-type sensor (as provided in U.S. patent application Ser. No. 11/444,577 to Fein et al., the specification of which is incorporated by reference in its entirety herein for all purposes).

TABLE 1

Potential Effects of Different Sources of Artifact for a D-25 Digit Sensor

| Type of Motion | $\Delta\alpha$ | $\Delta\eta$ | $\Delta P_{tiss}$ | boundaries | heterogeneity |
|---|---|---|---|---|---|
| Flexing | low | high | high | high | moderate |
| Scratching | low | high | high | low | low |
| Tapping | high | high | high | moderate | moderate |
| Squeezing/Pressing | low | high | high | moderate | moderate |
| Swinging | high | low | low | low | low |
| Rubbing | low | high | high | moderate | moderate |

TABLE 2

Potential Effects of Different Sources of Artifact for a RS-10 Forehead Sensor

| Type of Motion | $\Delta\alpha$ | $\Delta\eta$ | $\Delta P_{tiss}$ | boundaries | heterogeneity |
|---|---|---|---|---|---|
| Flexing | low | high | moderate | high | moderate |
| Scratching | — | — | — | — | — |
| Tapping | — | — | — | — | — |
| Squeezing/Pressing | low | high | high | low | low |
| Swinging | moderate | low | low | low | low |
| Rubbing | low | high | high | moderate | moderate |

TABLE 3

Potential Effects of Different Sources of Artifact for a Storm 1 Sensor

| Type of Motion | $\Delta\alpha$ | $\Delta\eta$ | $\Delta P_{tiss}$ | boundaries | heterogeneity |
|---|---|---|---|---|---|
| Flexing | low | low | high | low | low |
| Scratching | low | low | high | low | low |
| Tapping | high | low | high | low | low |
| Squeezing/Pressing | low | low | high | low | low |
| Swinging | high | low | low | low | low |
| Rubbing | low | low | high | low | low |

Monitors 90 that utilize signal processing algorithms such as the STORM algorithm may be able to overcome the effects of various types of signal artifacts. STORM sensors may include sensors designed to be used where "motion provides the signal", i.e., the cardiac pulse need not be present or discernible in order for the oximeter to provide $SpO_2$ values. Instead, the red and IR waveforms resulting from the motion itself are used for determining the arterial saturation. This feature is possible for tissue beds that are well "arterialized" (a large supply of arterial blood relative to the metabolic needs of the tissue) resulting in a small arterio-venous saturation difference, as well as other signal characteristics. It has been observed that the necessary degree of arterialization correlates well to being "well perfused" at the tissue site, which itself correlates well to the tissue bed being warm. Thus by monitoring the temperature of the skin at the sensor site, and by knowing a value of temperature (programmed into the memory chip) at which the "motion-is-signal" algorithm can be utilized for the specific sensor design being used, improved reading accuracy through motion can be better accomplished.

In particular, such algorithms may be effective in overcoming boundary condition artifacts and heterogeneity-based artifacts. When such algorithms are used in conjunction with sensors 10 that are able to switch from a reflectance-type configuration to a transmission-type configuration, or vice versa, the effects of certain types of artifacts may be further reduced. For example, certain types of $\Delta P_{tiss}$ artifacts may be less profound for reflectance-type configurations relative to transmission-type configurations. As such, sensors 10 as provided may include one or more temperature sensors configured to communicate with monitor 90 and provide temperature inputs to determine whether the STORM algorithm should used to process the incoming signal from sensor 10.

Further, signal quality metrics may be employed to determine if various types of signal artifacts are present in the incoming signal. For example, a tapping motion of a digit may present a characteristic signal artifact that may be identified by the monitor 90. If such an artifact is identified, a sensor 10 may then automatically switch from a transmission mode to a reflectance mode. In other embodiments, bending or flexing of a tissue site may result in blood flow and skin discoloration changes that have a characteristic artifact effect. In such an embodiment, the sensor 10 may switch modes until the signal artifact is resolved.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, fractional hemoglobin, intravascular dyes, and/or water content. Rather, the various embodiments may cover all modifications, equivalents, and alternatives falling within the spirit and scope of the disclosure as defined by the following appended claims.

What is claimed is:

1. A sensor comprising:
a sensor body adapted to be applied to a patient's tissue;
a first emitter and a second emitter disposed on the sensor body;
a detector disposed on the sensor body, wherein the first emitter and the detector are capable of operating in transmission mode and the second emitter and the detector are capable of operating in reflectance mode;
a switch disposed on the sensor body and coupled to the first emitter and the second emitter; and
a processor-based controller disposed on the sensor body and configured to receive an input from the detector, wherein the controller is configured to control the switch to alternate between activation of the first emitter and the second emitter based on the input.

2. The sensor, as set forth in claim 1, wherein the sensor comprises at least one of a pulse oximetry sensor or a sensor for measuring a water fraction.

3. The sensor, as set forth in claim 1, wherein first emitter or the second emitter comprises at least one light emitting diode and wherein the detector comprises at least one photodetector.

4. The sensor, as set forth in claim 1, wherein the first emitter and the detector are spaced apart about 20 mm to about 25 mm or wherein the second emitter and the detector are spaced apart about 8 mm to about 14 mm.

5. The sensor, as set forth in claim 1, wherein the controller is configured to receive a signal from the detector and detect a signal artifact in the signal.

6. The sensor, as set forth in claim 5, wherein the controller is configured to switch from transmission mode or reflectance mode if the controller detects the signal artifact.

7. The sensor, as set forth in claim 5, wherein the controller is configured to arbitrate between transmission mode and reflectance mode to mitigate the signal artifact in the signal.

8. The sensor, as set forth in claim 5, wherein the controller is configured to switch from reflectance mode to transmission mode in the presence of a signal artifact comprising a $\eta$-artifact.

9. The sensor, as set forth in claim 5, wherein the controller is configured to switch between reflectance mode and transmission mode during the time an $\alpha$-artifact or a $\Delta P_{tiss}$-artifact is detected.

10. The sensor, as set forth in claim 1, comprising an encoder, wherein the encoder comprises stored data related to the sensor.

11. A system comprising:
a sensor comprising:
a sensor body adapted to be applied to a patient's tissue;
a first emitter and a second emitter disposed on the sensor body;
a detector disposed on the sensor body, wherein the first emitter and the detector are capable of operating in transmission mode and the second emitter and the detector are capable of operating in reflectance mode, and wherein the sensor is capable of alternating between transmission mode and reflectance mode; and
a monitor comprising a processor configured to:
detect a signal artifact in a signal from the sensor;
determine a characteristic of the signal artifact; and
control the activation of the first emitter and the second emitter based on the characteristic of the signal artifact.

12. The system, as set forth in 11, wherein the sensor comprises at least one of a pulse oximetry sensor or a sensor for measuring water fraction.

13. The system, as set forth in claim 11, wherein the first emitter and the detector are spaced apart about 20 mm to about 25 mm or wherein the second emitter and the detector are spaced apart about 8 mm to about 14 mm.

14. The system, as set forth in claim 11, wherein the characteristic of the signal artifact comprises determining if the signal artifact comprises one or more of an $\eta$-artifact, $\alpha$-artifact, $\Delta P_{tiss}$-artifact, heterogeneity artifact, or boundary condition artifact.

15. The system, as set forth in claim 14, wherein the monitor is configured to determine a type of patient motion based on the presence of one or more of the $\eta$-artifact, $\alpha$-artifact, $\Delta P_{tiss}$-artifact, heterogeneity artifact, or boundary condition artifact.

16. The system, as set forth in claim 11, wherein the sensor comprises a switch disposed on the sensor body and coupled between the first emitter and the second emitter.

* * * * *